United States Patent
Commissiong et al.

(10) Patent No.: US 9,115,208 B2
(45) Date of Patent: Aug. 25, 2015

(54) DOPAMINERGIC NEURONAL SURVIVAL-PROMOTING FACTORS AND USES THEREOF

(75) Inventors: John W. Commissiong, Mississauga (CA); Andrei A. Raibekas, Toronto (CA)

(73) Assignee: AMARANTUS THERAPEUTICS, INC., San Francisco, CA (US)

( * ) Notice: Subject to any disclaimer, the term of this patent is extended or adjusted under 35 U.S.C. 154(b) by 0 days.

(21) Appl. No.: 13/305,025

(22) Filed: Nov. 28, 2011

(65) Prior Publication Data
US 2013/0078220 A1    Mar. 28, 2013

Related U.S. Application Data

(63) Continuation of application No. 12/535,029, filed on Aug. 4, 2009, now Pat. No. 8,084,425, which is a continuation of application No. 10/102,265, filed on Mar. 20, 2002, now abandoned.

(60) Provisional application No. 60/277,516, filed on Mar. 20, 2001.

(51) Int. Cl.
| | | |
|---|---|---|
| *A61K 38/18* | (2006.01) | |
| *A61K 35/30* | (2006.01) | |
| *C07K 14/475* | (2006.01) | |
| *G01N 33/50* | (2006.01) | |
| *A61K 38/00* | (2006.01) | |

(52) U.S. Cl.
CPC ............... *C07K 14/475* (2013.01); *A61K 35/30* (2013.01); *A61K 38/18* (2013.01); *A61K 38/185* (2013.01); *A61K 38/00* (2013.01); *G01N 33/5058* (2013.01)

(58) Field of Classification Search
None
See application file for complete search history.

(56) References Cited

U.S. PATENT DOCUMENTS

| | | |
|---|---|---|
| 8,084,425 B2 | 12/2011 | Commissiong et al. |
| 2002/0132978 A1 | 9/2002 | Gerber et al. |
| 2002/0182198 A1 | 12/2002 | Commissiong et al. |
| 2004/0006780 A1 | 1/2004 | Gerber et al. |
| 2006/0084619 A1 | 4/2006 | Saarma et al. |
| 2006/0195915 A1 | 8/2006 | Saarma et al. |
| 2010/0119491 A1 | 5/2010 | Commissiong et al. |
| 2011/0212055 A1 | 9/2011 | Commissiong |
| 2014/0243264 A1 | 8/2014 | Wen |

FOREIGN PATENT DOCUMENTS

| | | |
|---|---|---|
| WO | WO 01/19851 A2 | 3/2001 |
| WO | WO 01/25427 A1 | 4/2001 |
| WO | WO 01/19851 A3 | 9/2001 |
| WO | WO 01/70174 A2 | 9/2001 |
| WO | WO 02/074956 A2 | 9/2002 |
| WO | WO 02/074956 A3 | 7/2003 |
| WO | WO 2009/120810 A2 | 10/2009 |
| WO | WO 2009/133247 A1 | 11/2009 |
| WO | WO 2009/120810 A3 | 3/2010 |

OTHER PUBLICATIONS

Lindholm P et al. (2008) MANF is widely expressed in mammalian tissues and differently regulated after ischemic and epileptic insults in rodent brain. Mol. Cell. Neurosci. 39:356-371.*
Tang FI et al. (1998) Intranigral ventral mesencephalic grafts and nigrostriatal injections of glial cell line-derived neurotrophic factor restore dopamine release in the striatum of 6-hydroxydopamine-lesioned rats. Exp. Brain Res. 119:287-296.*
Takeshima T et al. (1994) Mesencephalic type 1 astrocytes rescue dopaminergic neurons from death induced by serum deprivation. J. Neurosci. 14(8):4769-4779.*
Voutilainen MH et al. (2009) Mesencephalic astrocyte-derived neurotrophic factor is neurorestorative in rat model of Parkinson's disease. J. Neurosci. 29(30):9651-9659.*
Airavaara, et al. CDNF protects the nigrostriatal dopamine system and promotes recovery after MPTP treatment in mice. Cell Transplant. 2012;21(6):1213-23. doi: 10.3727/096368911X600948. Epub Sep. 22, 2011.
Airavaara, et al. Endogenous GDNF in ventral tegmental area and nucleus accumbens does not play a role in the incubation of heroin craving. Addict Biol. Apr. 2011;16(2):261-72. doi: 10.1111/j.1369-1600.2010.00281.x. Epub Dec. 23, 2010.
Airavaara, et al. Mesencephalic astrocyte-derived neurotrophic factor reduces ischemic brain injury and promotes behavioral recovery in rats. J Comp Neurol. Jul. 1, 2009;515(1):116-24. doi: 10.1002/cne. 22039.
Airavaara, et al. Neurorestoration. Parkinsonism Relat Disord. Jan. 2012;18 Suppl 1:S143-6.
Airavaara, et al. Widespread cortical expression of MANF by AAV serotype 7: localization and protection against ischemic brain injury. Exp Neural. Sep. 2010;225(1):104-13. doi: 10.1016/j.expneurol. 2010.05.020. Epub Jun. 2, 2010.
Almutawaa, et al. Induction of neurotrophic and differentiation genes in neural stem cells by valproic acid. Program No. 633.24. 2012 Neuroscience Meeting Planner. New Orleans, LA: Society for Neuroscience, 2012. Online.
Andressoo, et al. Signalling mechanisms underlying development and maintenance of dopamine neurons. Curr Opin Neurobiol. Jun. 2008;18(3):297-306. doi: 10.1016/j.conb.2008.07.005.
Apostolou, et al. Armet, a UPR-upregulated protein, inhibits cell proliferation and ER stress-induced cell death. Exp Cell Res. Aug. 1, 2008;314(13):2454-67. doi: 10.1016/j.yexcr.2008.05.001. Epub May 13, 2008.
Back, et al. Gene therapy with AAV2-CDNF provides functional benefits in a rat model of Parkinson's disease. Brain Behav. Mar. 2013;3(2):75-88. doi: 10.1002/brb3.117. Epub Jan. 14, 2013.

(Continued)

*Primary Examiner* — Kimberly A Ballard
(74) *Attorney, Agent, or Firm* — Wilson Sonsini Goodrich & Rosati, P.C.

(57) ABSTRACT

In general, the invention features substantially purified MANF and substantially purified nucleic acids encoding the same. The invention also features a pharmaceutical composition that includes MANF and a pharmaceutically-acceptable excipient, methods for treatment of a neurodegenerative disease, methods for improving dopaminergic neuronal survival during or following cell transplantation, methods for production of neurons for transplantation, and methods for identifying compounds that modulate or mimic MANF's biological activity.

27 Claims, 11 Drawing Sheets

(56) References Cited

OTHER PUBLICATIONS

Barkholz. Charakterisierungsstudien der biologischen und neurotrophen Eigenschaften des cerebral dopamine neurotrophic factor (CDNF). University of Marburg, academic dissertation, 2012.
Bartus, et al. Bioactivity of AAV2-neurturin gene therapy (CERE-120): differences between Parkinson's disease and nonhuman primate brains. Mov Disord. Jan. 2011;26(1):27-36. doi: 10.1002/mds.23442. Epub Nov. 18, 2010.
Cameron, et al. Transcriptional profiling of chondrodysplasia growth plate cartilage reveals adaptive ER-stress networks that allow survival but disrupt hypertrophy. PLoS One. 2011;6(9):e24600. doi: 10.1371/journal.pone.0024600. Epub Sep. 15, 2011.
Chen, et al. MANF regulates dopaminergic neuron development in larval zebrafish. Dev Biol. Oct. 15, 2012;370(2):237-49. doi: 10.1016/j.ydbio.2012.07.030. Epub Aug. 7, 2012.
Choi, et al. Analysis of mutations and the association between polymorphisms in the cerebral dopamine neurotrophic factor (CDNF) gene and Parkinson disease. Neurosci Lett. Apr. 15, 2011;493(3):97-101. doi: 10.1016/j.neulet.2011.02.013. Epub Feb. 12, 2011.
Colla, et al. Endoplasmic reticulum stress is important for the manifestations of α-synucleinopathy in vivo. J Neurosci. Mar. 7, 2012;32(10):3306-20. doi: 10.1523/JNEUROSCI.5367-11.2012.
Evron, et al. Normal polymorphism in the incomplete trinucleotide repeat of the arginine-rich protein gene. Cancer Res. Jul. 15, 1997;57(14):2888-9.
Fonseca, et al. Stress hypERactivation in the β-cell. Islets. Jan.-Feb. 2010;2(1):1-9. doi: 10.4161/isl.2.1.10456.
Glembotski, et al. Mesencephalic astrocyte-derived neurotrophic factor protects the heart from ischemic damage and is selectively secreted upon sarco/endoplasmic reticulum calcium depletion. J Biol Chem. Jul. 27, 2012;287(31):25893-904. doi: 10.1074/jbc.M112.356345. Epub May 25, 2012.
Glembotski. Functions for the cardiomyokine, MANF, in cardioprotection, hypertrophy and heart failure. J Mol Cell Cardiol. Oct. 2011;51(4):512-7. doi: 10.1016/j.yjmcc.2010.10.008. Epub Oct. 21, 2010.
Grondin, et al. Chronic, controlled GDNF infusion promotes structural and functional recovery in advanced parkinsonian monkeys. Brain. Oct. 2002;125(Pt 10):2191-201.
Gyarfas, et al. Regulation of brain-derived neurotrophic factor (BDNF) and cerebral dopamine neurotrophic factor (CDNF) by antiparkinsonian drug theraCell Mol Neurobiol. Apr. 2010;30(3):361-8. doi: 10.1007/s10571-009-9458-3. Epub Sep. 24, 2009.py in vivo.
Hellman, et al. 1H, 13C and 15N resonance assignments of the human mesencephalic astrocyte-derived neurotrophic factor. Biomol NMR Assign. Oct. 2010;4(2):215-7. doi: 10.1007/s12104-010-9251-8. Epub Jul. 9, 2010.
Hellman, et al. Mesencephalic astrocyte-derived neurotrophic factor (MANF) has a unique mechanism to rescue apoptotic neurons. J Biol Chem. Jan. 28, 2011;286(4):2675-80. doi: 10.1074/jbc.M110.146738. Epub Nov. 3, 2010.
Henderson, et al. Mesencephalic astrocyte-derived neurotrophic factor (MANF) secretion and cell surface binding are modulated by KDEL receptors. J Biol Chem. Feb. 8, 2013;288(6):4209-25. doi: 10.1074/jbc.M112.400648. Epub Dec. 19, 2012.
Hoffer. Commentary on chronic infusion of CDNF prevents 6-OHDA-induced deficits in a rat model of Parkinson's disease. Merja H. Voutilainen et al. Exp Neurol. Aug. 2011;230(2):162-6. doi: 10.1016/j.expneurol.2011.04.015. Epub Apr. 30, 2011.
Hoseki, et al. Solution structure and dynamics of mouse ARMET. FEBS Lett. Apr. 16, 2010;584(8):1536-42. doi: 10.1016/j.febslet.2010.03.008. Epub Mar. 6, 2010.
Hovland, et al. Six-month continuous intraputamenal infusion toxicity study of recombinant methionyl human glial cell line-derived neurotrophic factor (r-metHuGDNF in rhesus monkeys. Toxicol Pathol. Dec. 2007;35(7):1013-29.
Huynh, The Parkinson's disease market. Nat Rev Drug Discov. Aug. 1, 2011;10(8):571-2. doi: 10.1038/nrd3515.
Latge, et al. (1)H-, (13)C- and (15)N—NMR assignment of the N-terminal domain of human cerebral dopamine neurotrophic factor (CDNF). Biomol NMR Assign. Apr. 2013;7(1):101-3. doi: 10.1007/s12104-012-9388-8. Epub Apr. 18, 2012.
Lee, et al. XBP-1 regulates a subset of endoplasmic reticulum resident chaperone genes in the unfolded protien response. Mol Cell Biol. Nov. 2003;23(21):7448-59.
Lindholm, et al. ER stress and neurodegenerative diseases. Cell Death Differ. Mar. 2006;13(3):385-92.
Lindholm, et al. MANF is widely expressed in mammalian tissues and differently regulated after ischemic and epileptic insults in rodent brain. Mol Cell Neurosci. Nov. 2008;39(3):356-71. doi: 10.1016/j.mcn.2008.07.016. Epub Jul. 30, 2008.
Lindholm, et al. Novel CDNF/MANF family of neurotrophic factors. Dev Neurobiol. Apr. 2010;70(5):360-71.
Lindholm. Novel CDNF/MANF protein family: Molecular structure, expression and neurotrophic activity. University of Helsinki, academic dissertation, 2009.
Lohoff, et al. Association analysis between polymorphisms in the conserved dopamine neurotrophic factor (CDNF) gene and cocaine dependence. Neurosci Lett. Apr. 10, 2009;453(3):199-203. doi: 10.1016/j.neulet.2009.02.026. Epub Feb. 21, 2009.
Martyniuk, et al. Protein targets of acrylamide adduct formation in cultured rat dopaminergic cells. Toxicol Lett. Jun. 7, 2013;219(3):279-87. doi: 10.1016/j.toxlet.2013.03.031. Epub Apr. 6, 2013.
Meissner, et al. Priorities in Parkinson's disease research. Nat Rev Drug Discov. May 2011;10(5):377-93. doi: 10.1038/nrd3430.
Mizobuchi, et al. ARMET is a soluble ER protein induced by the unfolded protein response via ERSE-II element. Cell Struct Funct. 2007;32(1):41-50. Epub May 14, 2007.
Niles, et al. Valproic acid up-regulates melatonin MT1 and MT2 receptors and neurotrophic factors CDNF and MANF in the rat brain. Int J Neuropsychopharmacol. Oct. 2012;15(9):1343-50. doi: 10.1017/S1461145711001969. Epub Jan. 16, 2012.
Nundlall, et al. An unfolded protein response is the initial cellular response to the expression of mutant matrilin-3 in a mouse model of multiple epiphyseal dysplasia. Cell Stress Chaperones. Nov. 2010;15(6):835-49. doi: 10.1007/s12192-010-0193-y. Epub Apr. 30, 2010.
Office action dated Mar. 19, 2013 for U.S. Appl. No. 12/934,454.
Oh-Hashi, et al. Intracellular trafficking and secretion of mouse mesencephalic astrocyte-derived neurotrophic factor. Mol Cell Biochem. Apr. 2012;363(1-2):35-41. doi: 10.1007/s11010-011-1155-0. Epub Nov. 27, 2011.
Olson, et al. On neonathal asphyxia: Clinical and animals studies including development of a simple, safe method for therapeutic hypothermia with global applicability. Karolinska Institute, academic dissertation, 2011.
Palgi, et al. Evidence that DmMANF is an invertebrate neurotrophic factor supporting dopaminergic neurons. Proc Natl Acad Sci U S A. Feb. 17, 2009;106(7):2429-34. doi: 10.1073/pnas.0810996106. Epub Jan. 22, 2009.
Palgi, et al. Gene expression analysis of Drosophilaa Manf mutants reveals perturbations in membrane traffic and major metabolic changes. BMC Genomics. Apr. 11, 2012;13:134. doi: 10.1186/1471-2164-13-134.
Parkash, et al. The structure of the conserved neurotrophic factors MANF and CDNF explains why they are bifunctional. Protein Eng Des Sel. Apr. 2009;22(4):233-41. doi: 10.1093/protein/gzn080. Epub Mar. 3, 2009.
Peck. Amgen decision to halt GDNF clinical trials and withdraw the drug triggers protest from researchers and patients. Neurology Today Apr. 2005-vol. 5-Issue 4-pp. 4,7,24.
Piepoli, et al. Lack of association between UGT1A7, UGT1A9, ARP, SPINK1 and CFTR gene polymorphisms and pancreatic cancer in Italian patients. World J Gastroenterol. Oct. 21, 2006;12(39):6343-8.
Ren. Program No. 651.13. 2012 Neuroscience Meeting Planner. New Orleans, LA: Society for Neuroscience, 2012. Online.
Renko. Nerve growth factors structure, mechanisms of action and brain distribution. New neurotrophic factors CDNF and MANF's effects in rat brain neurotransmission studied by microdialysis. University of Helsinki, academic dissertation, 2012. (abstract only).

(56) References Cited

OTHER PUBLICATIONS

Rocha, et al. Astrocyte-derived GDNF is a potent inhibitor of microglial activation. Neurobiol Dis. Sep. 2012;47(3):407-15. doi: 10.1016/j.nbd.2012.04.014. Epub May 3, 2012.
Sadighi, et al. Heightened induction of proapoptotic signals in response to endoplasmic reticulum stress in primary fibroblasts from a mouse model of longevity. J Biol Chem. Sep. 2, 2011;286(35):30344-51. doi: 10.1074/jbc.M111.220541. Epub Jul. 12, 2011.
Savaskan, et al. Brain miffed by macrophage migration inhibitory factor. Int J Cell Biol. 2012;2012:139573. doi: 10.1155/2012/139573. Epub Sep. 3, 2012.
Shen, et al. Upregulation of mesencephalic astrocyte-derived neurotrophic factor in glial cells is associated with ischemia-induced glial activation. J Neuroinflammation. Nov. 23, 2012;9:254. doi: 10.1186/1742-2094-9-254.
Shridhar, et al. Mutations in the arginine-rich protein gene (ARP) in pancreatic cancer. Oncogene. May 8, 1997;14(18):2213-6.
Shridhar, et al. Mutations in the arginine-rich protein gene, in lung, breast, and prostate cancers, and in squamous cell carcinoma of the head and neck. Cancer Res. Dec. 15, 1996;56(24):5576-8.
Slevin, et al. Improvement of bilateral motor functions in patients with Parkinson disease through the unilateral intraputaminal infusion of glial cell line-derived neurotrophic factor. J Neurosurg. Feb. 2005;102(2):216-22.
Sun, et al. Intracellular trafficking and secretion of cerebral dopamine neurotrophic factor in neurosecretory cells. J Neurochem. Apr. 2011;117(1):121-32. doi: 10.1111/j.1471-4159.2011.07179.x. Epub Feb. 9, 2011.
Tadimalla, et al. Mesencephalic astrocyte-derived neurotrophic factor is an ischemia-inducible secreted endoplasmic reticulum stress response protein in the heart. Res. Nov. 21, 2008;103(11):1249-58. doi: 10.1161/CIRCRESAHA.108.180679. Epub Oct. 16, 2008.
Tanaka, et al. Polymorphic variation of the ARP gene on 3p21 in Japanese esophageal cancer patients. Oncol Rep. May-Jun. 2000;7(3):591-3.
Vilponen, et al. Novel neurotrophic factors MANF and CDNF protect neurons in primary culture. Eur J Pharm Sci. 34S (2008) S30-S41; doi:10.1016/j.ejps.2008.02.092, conference abstract.
Voutilainen, et al. Chronic infusion of CDNF prevents 6-OHDA-induced deficits in a rat model of Parkinson's disease. Exp Neurol. Mar. 2011;228(1):99-108. doi: 10.1016/j.expneurol.2010.12.013. Epub Dec. 24, 2010.
Wang, et al. Altered expression of Armet and Mrlp51 in the oocyte, preimplantation embryo, and brain of mice following oocyte in vitro maturation but postnatal brain development and cognitive function are normal. Reproduction. Sep. 2011;142(3):401-8. doi: 10.1530/Rep-11-0152. Epub Jul. 5, 2011.
Yang, et al. A novel mechanism for the specific neuropathology in a conditional knock-in mouse model of Spinocerebellar Ataxia 17. Program No. 547.09. 2012 Neuroscience Meeting Planner. New Orleans, LA: Society for Neuroscience, 2012. Online.
Yu, et al. Induction profile of MANF/ARMET by cerebral ischemia and its implication for neuron protection. J Cereb Blood Flow Metab. Jan. 2010;30(1):79-91. doi: 10.1038/jcbfm.2009.181. Epub Sep. 23, 2009.
Apfel. Neurotrophic factor therapy—prospects and problems. Clin Chem Lab Med. Apr. 2001;39(4):351-5. Abstract only.
Bjorklund, et al. Studies on neuroprotective and regenerative effects of GDNF in a partial lesion model of Parkinson's disease. Neurobiol Dis. 1997;4(3-4):186-200.
Collier, et al. Cellular models to study dopaminergic injury responses. Ann N Y Acad Sci. Jun. 2003;991:140-51. Abstract only.
Czarkowska-Bauch, et al. The prospects for clinical use of neurotrophins in therapy. Neurol Neurochir Pol. May-Jun. 2003;37(3):523-36. Abstract only.
Dauer. Neurotrophic factors and Parkinson's disease: the emergence of a new player? Sci STKE. Nov. 6, 2007;2007(411):pe60.
EBI Database. Accession No. BD539164. Aug. 27, 2002.

European office action dated Dec. 3, 2012 for Application No. 09724166.5.
European search report dated Feb. 17, 2011 for Application No. 09724166.5.
Gill, et al. Direct brain infusion of glial cell line-derived neurotrophic factor in Parkinson disease. Nat Med. May 2003;9(5):589-95. Epub Mar. 31, 2003.
Golembieski, et al. Accession No. S27956. 1997.
Hong, et al. GDNF therapy for Parkinson's disease. Expert Rev Neurother. Jul. 2008;8(7):1125-39.
International Search Report and Written Opinion dated Nov. 22, 2010 for PCT/US2010/050438.
International Search Report dated Dec. 4, 2009 for PCT/2009/038306.
Lang, et al. Randomized controlled trial of intraputamenal glial cell line-derived neurotrophic factor infusion in Parkinson disease. Ann Neurol. Mar. 2006;59(3):459-66.
Lindholm, et al. Novel neurotrophic factor CDNF protects and rescues midbrain dopamine neurons in vivo. Nature. Jul. 5, 2007;448(7149):73-7.
Marks, et al. Gene delivery of AAV2-neurturin for Parkinson's disease: a double-blind, randomised, controlled trial. Lancet Neurol. Dec. 2010;9(12):1164-72. Epub Oct. 20, 2010.
Mayer, et al. Basic fibroblast growth factor promotes the survival of embryonic ventral mesencephalic dopaminergic neurons—I. Effects in vitro. Neuroscience. Sep. 1993;56(2):379-88.
Mayer, et al. Basic fibroblast growth factor promotes the survival of embryonic ventral mesencephalic dopaminergic neurons—II. Effects on nigral transplants in vivo. Neuroscience. Sep. 1993;56(2):389-98.
Office action dated Feb. 2, 2011 for U.S. Appl. No. 12/535,029.
Office action dated Apr. 28, 2006 for U.S. Appl. No. 10/102,265.
Panchision, et al. An immortalized, type-1 astrocyte of mesencephalic origin source of a dopaminergic neurotrophic factor. J Mol Neurosci. Dec. 1998;11(3):209-21.
Patel, et al. Intraputamenal infusion of glial cell line-derived neurotrophic factor in PD: a two-year outcome study. Ann Neurol. Feb. 2005;57(2):298-302.
Peaire, et al. Production of dopaminergic neurons for cell therapy in the treatment of Parkinson's disease. J Neurosci Methods. Mar. 30, 2003;124(1):61-74. Abstract only.
Petrova, et al. Discovering novel phenotype-selective neurotrophic factors to treat neurodegenerative diseases. Prog Brain Res. 2004;146:168-83.
Petrova, et al. MANF: a new mesencephalic, astrocyte-derived neurotrophic factor with selectivity for dopaminergic neurons. J Mol Neurosci. Apr. 2003;20(2):173-88.
Richardson. Neuroprotective agents. Phys Med Rehabil Clin N Am. May 1999;10(2):447-61. Abstract only.
Shridar, et al. A gene from human chromosomal band 3p21.1 encodes a highly conserved arginine-rich protein and is mutated in renal cell carcinomas. Oncogene. May 2, 1996;12(9):1931-9.
Voutilainen, et al. Mesencephalic astrocyte-derived neurotrophic factor is neurorestorative in rat model of Parkinson's disease. J Neurosci. Jul. 29, 2009;29(30):9651-9.
Winkler, et al. Short-term GDNF treatment provides long-term rescue of lesioned nigral dopaminergic neurons in a rat model of Parkinson's disease. J Neurosci. Nov. 15, 1996;16(22):7206-15.
Zhou, et al. Mesencephalic astrocyte-derived neurotrophic factor enhances nigral gamma-aminobutyric acid release. Neuroreport. Feb. 27, 2006;17(3):293-7.
Office action dated Jan. 20, 2015 for U.S. Appl. No. 14/124,802.
Bannon, et al. Pharmacology of mesocortical dopamine neurons. Pharmacol Rev. Mar. 1983;35(1):53-68.
Bunney, et al. Midbrain dopamine system electrophysiological functioning: a review and new hypothesis. Synapse. Oct. 1991;9(2):79-94.
Bushong, et al. Protoplasmic astrocytes in CA1 stratum radiatum occupy separate anatomical domains. J Neurosci. Jan. 1, 2002;22(1):183-92.
Chiocco, et al. Neurotrophic factors for the treatment of Parkinson's disease. Parkinsonism Relat Disord. 2007;13 Suppl 3:S321-8. doi: 10.1016/S1353-8020(08)70024-5.

(56) References Cited

OTHER PUBLICATIONS

Hoyt, et al. Head injury: an immunologic deficit in T-cell activation. J Trauma. Jul. 1990;30(7):759-66; discussion 766-7.
International search report and written opinion dated Sep. 3, 2014 for PCT/US2014/043506.
International search report and written opinion dated Dec. 16, 2013 for PCT/US2013/066688.
Morgan, et al. Dissociation of crossed and uncrossed nigrostriatal projections with respect to site of origin in the rat. Neuroscience. Mar. 1986;17(3):609-14.
Neuhoff, et al. I(h) channels contribute to the different functional properties of identified dopaminergic subpopulations in the midbrain. J Neurosci. Feb. 15, 2002;22(4):1290-302.
Notice of allowance dated Sep. 26, 2011 for U.S. Appl. No. 12/535,029.
Office action dated Apr. 23, 2014 for U.S. Appl. No. 12/934,454.
Office action dated Nov. 8, 2013 for U.S. Appl. No. 12/934,454.
Office action dated Nov. 24, 2014 for U.S. Appl. No. 12/934,454.
Quattrocchi, et al. Suppression of cellular immune activity following severe head injury. J Neurotrauma. 1990 Summer;7(2):77-87.
Shimoda, et al. A high percentage yield of tyrosine hydroxylase-positive cells from rat E14 mesencephalic cell culture. Brain Res. Jul. 24, 1992;586(2):319-31.
Weiss-Wunder, et al. Subpopulations of mesencephalic dopaminergic neurons express different levels of tyrosine hydroxylase messenger RNA. J Comp Neurol. Jan. 15, 1991;303(3):478-88.

* cited by examiner

FIGURE 2

```
MGKWHVGGRR GAPRQWGATA RGRDLEAVRR GGCGSVGRRR QRRRRRRRRM
RRMRRMWATQ GLAVALALSV LPGSRALRPG DCEVCISYLG RFYQDLKDRD
VTFSPATIEN ELIKFCREAR GKENRLCYYI GATDDAATKI INEVSKPLAH
HIPVEKICEK LKKKDSQICE LKYDKQIDLS TVDLKKLRVK ELKKILDDWG
ETCKGCAEKS DYIRKINELM PKYAPKAASA PTDL (SEQ ID NO: 1)

MWATQGLAVA LALSVLPGSR ALRPGDCEVC ISYLGRFYQD LKDRDVTFSP
ATIENELIKF CREARGKENR LCYYIGATDD AATKIINEVS KPLAHHIPVE
KICEKLKKKD SQICELKYDK QIDLSTVDLK KLRVKELKKI LDDWGETCKG
CAEKSDYIRK INELMPKYAP KAASAPTDL (SEQ ID NO: 2)

LRPGDCEVCI SYLGRFYQDL KDRDVTFSPA TIENELIKFC REARGKENRL
CYYIGATDDA ATKIINEVSK PLAHHIPVEK ICEKLKKKDS QICELKYDKQ
IDLSTVDLKK LRVKELKKIL DDWGETCKGC AEKSDYIRKI NELMPKYAPK
AASAPTDL (SEQ ID NO: 3)

MLRPGDCEVC ISYLGRFYQD LKDRDVTFSP ATIENELIKF CREARGKENR
LCYYIGATDD AATKIINEVS KPLAHHIPVE KICEKLKKKD SQICELKYDK
QIDLSTVDLK KLRVKELKKI LDDWGETCKG CAEKSDYIRK INELMPKYAP
KAASAPTDL (SEQ ID NO: 4)
```

FIGURE 3

```
MWATRGLAVA LALSVLPDSR ALRPGDCEVC ISYLGRFYQD LKDRDVTFSP
ATIEEELIKF CREARGKENR LCYYIGATDD AATKIINEVS KPLAHHIPVE
KICEKLKKKD SQICELKYDK QIDLSTVDLK KLRVKELKKI LDDWGEMCKG
CAEKSDYIRK INELMPKYAP KAASARTDL (SEQ ID NO: 5)

LRPGDCEVCI SYLGRFYQDL KDRDVTFSPA TIEEELIKFC REARGKENRL
CYYIGATDDA ATKIINEVSK PLAHHIPVEK ICEKLKKKDS QICELKYDKQ
IDLSTVDLKK LRVKELKKIL DDWGEMCKGC AEKSDYIRKI NELMPKYAPK
AASARTDL (SEQ ID NO: 6)

MLRPGDCEVC ISYLGRFYQD LKDRDVTFSP ATIEEELIKF CREARGKENR
LCYYIGATDD AATKIINEVS KPLAHHIPVE KICEKLKKKD SQICELKYDK
QIDLSTVDLK KLRVKELKKI LDDWGEMCKG CAEKSDYIRK INELMPKYAP
KAASARTDL (SEQ ID NO: 7)
```

FIGURE 4

```
atggggaagt ggcatgtggg agggcgccgg ggggcccccc gccaatgggg agctacggcg
cgcggccggg acttggaggc ggtgcggcgc ggcgggtgcg gttcagtcgg tcgcggcgg
cagcggagga ggaggaggag gaggaggatg aggaggatga ggaggatgtg ggccacgcag
gggctggcgg tggcgctggc tctgagcgtg ctgccggca gccgggcgct gcggccgggc
gactgcgaag tttgtatttc ttatctggga agatttacc aggacctcaa agacagagat
gtcacattct caccagccac tattgaaaac gaacttataa agttctgccg ggaagcaaga
ggcaaagaga atcggttgtg ctactatatc ggggccacag atgatgcagc caccaaaatc
atcaatgagg tatcaaagcc tctggcccac cacatccctg tggagaagat ctgtgagaag
cttaagaaga aggacagcca gatatgtgag cttaagtatg acaagcagat cgacctgagc
acagtggacc tgaagaagct ccgagttaaa gagctgaaga agattctgga tgactggggg
gagacatgca aaggctgtgc agaaaagtct gactacatcc ggaagataaa tgaactgatg
cctaaatatg cccccaaggc agccagtgca ccgaccgatt tgtag (SEQ ID NO: 8)

atgtgggcca cgcaggggct ggcggtggcg ctggctctga gcgtgctgcc gggcagccgg
gcgctgcggc cgggcgactg cgaagtttgt atttcttatc tgggaagatt ttaccaggac
ctcaaagaca gagatgtcac attctcacca gccactattg aaaacgaact tataaagttc
tgccgggaag caagaggcaa agagaatcgg ttgtgctact atatcggggc cacagatgat
gcagccacca aaatcatcaa tgaggtatca aagcctctgg cccaccacat ccctgtggag
aagatctgtg agaagcttaa gaagaggac agccagatat gtgagcttaa gtatgacaag
cagatcgacc tgagcacagt ggacctgaag aagctccgag ttaaagagct gaagaagatt
ctggatgact ggggggagac atgcaaaggc tgtgcagaaa agtctgacta catccggaag
ataaatgaac tgatgcctaa atatgcccc aaggcagcca gtgcaccgac cgatttgtag
(SEQ ID NO: 9)

atgctgcggc cgggcgactg cgaagtttgt atttcttatc tgggaagatt ttaccaggac
ctcaaagaca gagatgtcac attctcacca gccactattg aaaacgaact tataaagttc
tgccgggaag caagaggcaa agagaatcgg ttgtgctact atatcggggc cacagatgat
gcagccacca aaatcatcaa tgaggtatca aagcctctgg cccaccacat ccctgtggag
aagatctgtg agaagcttaa gaagaggac agccagatat gtgagcttaa gtatgacaag
cagatcgacc tgagcacagt ggacctgaag aagctccgag ttaaagagct gaagaagatt
ctggatgact ggggggagac atgcaaaggc tgtgcagaaa agtctgacta catccggaag
ataaatgaac tgatgcctaa atatgcccc aaggcagcca gtgcaccgac cgatttgtag
(SEQ ID NO: 10)
```

FIGURE 11A

Bovine pro-MANF

MWATHGLAVA LALSVLPASR ALRQGDCEVC ISYLGRFYQD LKDRDVTFSP ASIEKELIKF
CREARGKENR LCYYIGATED AATKIINEVS KPLSHHIPVE KICEKLKKD SQICELKYDK
QIDLSTVDLK KLRVKELKKI LDDWGETCKG CAEKSDYIRK INELMPKYAP KAASSRTDL
(SEQ ID NO: 14)

FIGURE 11B

Pig pro-MANF

MWFTHGLAVA LALSVLPASR ALRPGDCEVC ISYLGRFYQD LKDRDVTFSP ASIEKELTKF
CREARGKENR LCYYIGATDD AATKIINEVS KPLAHHIPVE KICEKLMKKD SQICELKYDK
QIDLSTVDLK KLRVKELKKI LDDWGETCXG CAEKSDYIRK INELMPKYAP KAASSRTDL
(SEQ ID NO: 15)

SEQUENCE LISTING

```
<160> NUMBER OF SEQ ID NOS: 17

<210> SEQ ID NO 1
<211> LENGTH: 234
<212> TYPE: PRT
<213> ORGANISM: Homo sapiens

<400> SEQUENCE: 1

Met Gly Lys Trp His Val Gly Gly Arg Arg Gly Ala Pro Arg Gln Trp
 1               5                  10                  15

Gly Ala Thr Ala Arg Gly Arg Asp Leu Glu Ala Val Arg Arg Gly Gly
                20                  25                  30

Cys Gly Ser Val Gly Arg Arg Arg Gln Arg Arg Arg Arg Arg Arg Arg
            35                  40                  45

Arg Met Arg Arg Met Arg Arg Met Trp Ala Thr Gln Gly Leu Ala Val
    50                  55                  60

Ala Leu Ala Leu Ser Val Leu Pro Gly Ser Arg Ala Leu Arg Pro Gly
65                  70                  75                  80

Asp Cys Glu Val Cys Ile Ser Tyr Leu Gly Arg Phe Tyr Gln Asp Leu
                85                  90                  95

Lys Asp Arg Asp Val Thr Phe Ser Pro Ala Thr Ile Glu Asn Glu Leu
            100                 105                 110

Ile Lys Phe Cys Arg Glu Ala Arg Gly Lys Glu Asn Arg Leu Cys Tyr
        115                 120                 125

Tyr Ile Gly Ala Thr Asp Asp Ala Ala Thr Lys Ile Ile Asn Glu Val
    130                 135                 140

Ser Lys Pro Leu Ala His His Ile Pro Val Glu Lys Ile Cys Glu Lys
145                 150                 155                 160

Leu Lys Lys Lys Asp Ser Gln Ile Cys Glu Leu Lys Tyr Asp Lys Gln
                165                 170                 175

Ile Asp Leu Ser Thr Val Asp Leu Lys Lys Leu Arg Val Lys Glu Leu
            180                 185                 190

Lys Lys Ile Leu Asp Asp Trp Gly Glu Thr Cys Lys Gly Cys Ala Glu
        195                 200                 205

Lys Ser Asp Tyr Ile Arg Lys Ile Asn Glu Leu Met Pro Lys Tyr Ala
    210                 215                 220

Pro Lys Ala Ala Ser Ala Pro Thr Asp Leu
225                 230

<210> SEQ ID NO 2
<211> LENGTH: 179
<212> TYPE: PRT
<213> ORGANISM: Homo sapiens

<400> SEQUENCE: 2

Met Trp Ala Thr Gln Gly Leu Ala Val Ala Leu Ala Leu Ser Val Leu
 1               5                  10                  15

Pro Gly Ser Arg Ala Leu Arg Pro Gly Asp Cys Glu Val Cys Ile Ser
```

```
            20                  25                  30
Tyr Leu Gly Arg Phe Tyr Gln Asp Leu Lys Asp Arg Asp Val Thr Phe
                35                  40                  45

Ser Pro Ala Thr Ile Glu Asn Glu Leu Ile Lys Phe Cys Arg Glu Ala
 50                  55                  60

Arg Gly Lys Glu Asn Arg Leu Cys Tyr Tyr Ile Gly Ala Thr Asp Asp
 65                  70                  75                  80

Ala Ala Thr Lys Ile Ile Asn Glu Val Ser Lys Pro Leu Ala His His
                 85                  90                  95

Ile Pro Val Glu Lys Ile Cys Glu Lys Leu Lys Lys Asp Ser Gln
                100                 105                 110

Ile Cys Glu Leu Lys Tyr Asp Lys Gln Ile Asp Leu Ser Thr Val Asp
            115                 120                 125

Leu Lys Lys Leu Arg Val Lys Glu Leu Lys Lys Ile Leu Asp Asp Trp
        130                 135                 140

Gly Glu Thr Cys Lys Gly Cys Ala Glu Lys Ser Asp Tyr Ile Arg Lys
145                 150                 155                 160

Ile Asn Glu Leu Met Pro Lys Tyr Ala Pro Lys Ala Ala Ser Ala Pro
                165                 170                 175

Thr Asp Leu

<210> SEQ ID NO 3
<211> LENGTH: 158
<212> TYPE: PRT
<213> ORGANISM: Homo sapiens

<400> SEQUENCE: 3

Leu Arg Pro Gly Asp Cys Glu Val Cys Ile Ser Tyr Leu Gly Arg Phe
  1               5                  10                  15

Tyr Gln Asp Leu Lys Asp Arg Asp Val Thr Phe Ser Pro Ala Thr Ile
                 20                  25                  30

Glu Asn Glu Leu Ile Lys Phe Cys Arg Glu Ala Arg Gly Lys Glu Asn
             35                  40                  45

Arg Leu Cys Tyr Tyr Ile Gly Ala Thr Asp Asp Ala Ala Thr Lys Ile
 50                  55                  60

Ile Asn Glu Val Ser Lys Pro Leu Ala His His Ile Pro Val Glu Lys
 65                  70                  75                  80

Ile Cys Glu Lys Leu Lys Lys Asp Ser Gln Ile Cys Glu Leu Lys
                 85                  90                  95

Tyr Asp Lys Gln Ile Asp Leu Ser Thr Val Asp Leu Lys Lys Leu Arg
                100                 105                 110

Val Lys Glu Leu Lys Lys Ile Leu Asp Asp Trp Gly Glu Thr Cys Lys
            115                 120                 125

Gly Cys Ala Glu Lys Ser Asp Tyr Ile Arg Lys Ile Asn Glu Leu Met
        130                 135                 140

Pro Lys Tyr Ala Pro Lys Ala Ala Ser Ala Pro Thr Asp Leu
145                 150                 155

<210> SEQ ID NO 4
<211> LENGTH: 159
<212> TYPE: PRT
<213> ORGANISM: Artificial Sequence
<220> FEATURE:
<223> OTHER INFORMATION: based on Homo sapiens

<400> SEQUENCE: 4
```

```
Met Leu Arg Pro Gly Asp Cys Glu Val Cys Ile Ser Tyr Leu Gly Arg
1               5                   10                  15

Phe Tyr Gln Asp Leu Lys Asp Arg Asp Val Thr Phe Ser Pro Ala Thr
            20                  25                  30

Ile Glu Asn Glu Leu Ile Lys Phe Cys Arg Glu Ala Arg Gly Lys Glu
            35                  40                  45

Asn Arg Leu Cys Tyr Tyr Ile Gly Ala Thr Asp Ala Ala Thr Lys
50                  55                  60

Ile Ile Asn Glu Val Ser Lys Pro Leu Ala His His Ile Pro Val Glu
65                  70                  75                  80

Lys Ile Cys Glu Lys Leu Lys Lys Asp Ser Gln Ile Cys Glu Leu
                85                  90                  95

Lys Tyr Asp Lys Gln Ile Asp Leu Ser Thr Val Asp Leu Lys Lys Leu
            100                 105                 110

Arg Val Lys Glu Leu Lys Lys Ile Leu Asp Asp Trp Gly Glu Thr Cys
            115                 120                 125

Lys Gly Cys Ala Glu Lys Ser Asp Tyr Ile Arg Lys Ile Asn Glu Leu
            130                 135                 140

Met Pro Lys Tyr Ala Pro Lys Ala Ala Ser Ala Pro Thr Asp Leu
145                 150                 155

<210> SEQ ID NO 5
<211> LENGTH: 179
<212> TYPE: PRT
<213> ORGANISM: Mus musculus

<400> SEQUENCE: 5

Met Trp Ala Thr Arg Gly Leu Ala Val Ala Leu Ala Leu Ser Val Leu
1               5                   10                  15

Pro Asp Ser Arg Ala Leu Arg Pro Gly Asp Cys Glu Val Cys Ile Ser
            20                  25                  30

Tyr Leu Gly Arg Phe Tyr Gln Asp Leu Lys Asp Arg Asp Val Thr Phe
            35                  40                  45

Ser Pro Ala Thr Ile Glu Glu Leu Ile Lys Phe Cys Arg Glu Ala
50                  55                  60

Arg Gly Lys Glu Asn Arg Leu Cys Tyr Tyr Ile Gly Ala Thr Asp Asp
65                  70                  75                  80

Ala Ala Thr Lys Ile Ile Asn Glu Val Ser Lys Pro Leu Ala His His
                85                  90                  95

Ile Pro Val Glu Lys Ile Cys Glu Lys Leu Lys Lys Lys Asp Ser Gln
            100                 105                 110

Ile Cys Glu Leu Lys Tyr Asp Lys Gln Ile Asp Leu Ser Thr Val Asp
            115                 120                 125

Leu Lys Lys Leu Arg Val Lys Glu Leu Lys Lys Ile Leu Asp Asp Trp
130                 135                 140

Gly Glu Met Cys Lys Gly Cys Ala Glu Lys Ser Asp Tyr Ile Arg Lys
145                 150                 155                 160

Ile Asn Glu Leu Met Pro Lys Tyr Ala Pro Lys Ala Ala Ser Ala Arg
            165                 170                 175

Thr Asp Leu

<210> SEQ ID NO 6
<211> LENGTH: 158
<212> TYPE: PRT
<213> ORGANISM: Mus musculus
```

```
<400> SEQUENCE: 6

Leu Arg Pro Gly Asp Cys Glu Val Cys Ile Ser Tyr Leu Gly Arg Phe
  1               5                  10                  15

Tyr Gln Asp Leu Lys Asp Arg Asp Val Thr Phe Ser Pro Ala Thr Ile
             20                  25                  30

Glu Glu Glu Leu Ile Lys Phe Cys Arg Glu Ala Arg Gly Lys Glu Asn
         35                  40                  45

Arg Leu Cys Tyr Tyr Ile Gly Ala Thr Asp Asp Ala Ala Thr Lys Ile
     50                  55                  60

Ile Asn Glu Val Ser Lys Pro Leu Ala His His Ile Pro Val Glu Lys
 65                  70                  75                  80

Ile Cys Glu Lys Leu Lys Lys Asp Ser Gln Ile Cys Glu Leu Lys
                 85                  90                  95

Tyr Asp Lys Gln Ile Asp Leu Ser Thr Val Asp Leu Lys Leu Arg
             100                 105                 110

Val Lys Glu Leu Lys Lys Ile Leu Asp Asp Trp Gly Glu Met Cys Lys
         115                 120                 125

Gly Cys Ala Glu Lys Ser Asp Tyr Ile Arg Lys Ile Asn Glu Leu Met
     130                 135                 140

Pro Lys Tyr Ala Pro Lys Ala Ala Ser Ala Arg Thr Asp Leu
145                 150                 155

<210> SEQ ID NO 7
<211> LENGTH: 159
<212> TYPE: PRT
<213> ORGANISM: Artificial Sequence
<220> FEATURE:
<223> OTHER INFORMATION: based on Mus musculus

<400> SEQUENCE: 7

Met Leu Arg Pro Gly Asp Cys Glu Val Cys Ile Ser Tyr Leu Gly Arg
  1               5                  10                  15

Phe Tyr Gln Asp Leu Lys Asp Arg Asp Val Thr Phe Ser Pro Ala Thr
             20                  25                  30

Ile Glu Glu Glu Leu Ile Lys Phe Cys Arg Glu Ala Arg Gly Lys Glu
         35                  40                  45

Asn Arg Leu Cys Tyr Tyr Ile Gly Ala Thr Asp Asp Ala Ala Thr Lys
     50                  55                  60

Ile Ile Asn Glu Val Ser Lys Pro Leu Ala His His Ile Pro Val Glu
 65                  70                  75                  80

Lys Ile Cys Glu Lys Leu Lys Lys Asp Ser Gln Ile Cys Glu Leu
                 85                  90                  95

Lys Tyr Asp Lys Gln Ile Asp Leu Ser Thr Val Asp Leu Lys Lys Leu
             100                 105                 110

Arg Val Lys Glu Leu Lys Lys Ile Leu Asp Asp Trp Gly Glu Met Cys
         115                 120                 125

Lys Gly Cys Ala Glu Lys Ser Asp Tyr Ile Arg Lys Ile Asn Glu Leu
     130                 135                 140

Met Pro Lys Tyr Ala Pro Lys Ala Ala Ser Ala Arg Thr Asp Leu
145                 150                 155

<210> SEQ ID NO 8
<211> LENGTH: 705
<212> TYPE: DNA
<213> ORGANISM: Homo sapiens

<400> SEQUENCE: 8
```

```
atgggaagt ggcatgtggg agggcgccgg ggggccccc gccaatgggg agctacggcg      60
cgcggccggg acttggaggc ggtgcggcgc ggcgggtgcg gttcagtcgg tcggcggcgg     120
cagcggagga ggaggaggag gaggaggatg aggaggatga ggaggatgtg gccacgcag     180 gggctggcgg tggcgctggc tctgagcgtg ctgccgggca gccgggcgct gcggccgggc     240
gactgcgaag tttgtatttc ttatctggga agattttacc aggacctcaa agacagagat     300
gtcacattct caccagccac tattgaaaac gaacttataa agttctgccg ggaagcaaga     360
ggcaaagaga atcggttgtg ctactatatc ggggccacag atgatgcagc caccaaaatc     420
atcaatgagg tatcaaagcc tctggcccac cacatccctg tggagaagat ctgtgagaag     480
cttaagaaga aggacagcca gatatgtgag cttaagtatg acaagcagat cgacctgagc     540
acagtggacc tgaagaagct ccgagttaaa gagctgaaga agattctgga tgactgggg      600 gagacatgca aaggctgtgc agaaaagtct gactacatcc ggaagataaa tgaactgatg     660
cctaaatatg cccccaaggc agccagtgca ccgaccgatt tgtag                     705
```

<210> SEQ ID NO 9
<211> LENGTH: 540
<212> TYPE: DNA
<213> ORGANISM: Homo sapiens

<400> SEQUENCE: 9

```
atgtgggcca cgcaggggct ggcggtggcg ctggctctga gcgtgctgcc gggcagccgg      60
gcgctgcggc cgggcgactg cgaagtttgt atttcttatc tgggaagatt ttaccaggac    120
ctcaaagaca gagatgtcac attctcacca gccactattg aaaacgaact tataaagttc    180
tgccgggaag caagaggcaa agagaatcgg ttgtgctact atatcggggc cacagatgat    240
gcagccacca aaatcatcaa tgaggtatca aagcctctgg ccaccacat ccctgtggag    300 aagatctgtg agaagcttaa gaagaggac agccagatat gtgagcttaa gtatgacaag    360
cagatcgacc tgagcacagt ggacctgaag aagctccgag ttaaagagct gaagaagatt    420
ctggatgact gggggagac atgcaaaggc tgtgcagaaa agtctgacta catccggaag    480
ataaatgaac tgatgcctaa atatgccccc aaggcagcca gtgcaccgac cgatttgtag    540
```

<210> SEQ ID NO 10
<211> LENGTH: 480
<212> TYPE: DNA
<213> ORGANISM: Homo sapiens

<400> SEQUENCE: 10

```
atgctgcggc cgggcgactg cgaagtttgt atttcttatc tgggaagatt ttaccaggac      60
ctcaaagaca gagatgtcac attctcacca gccactattg aaaacgaact tataaagttc    120
tgccgggaag caagaggcaa agagaatcgg ttgtgctact atatcggggc cacagatgat    180
gcagccacca aaatcatcaa tgaggtatca aagcctctgg ccaccacat ccctgtggag    240 aagatctgtg agaagcttaa gaagaggac agccagatat gtgagcttaa gtatgacaag    300
cagatcgacc tgagcacagt ggacctgaag aagctccgag ttaaagagct gaagaagatt    360
ctggatgact gggggagac atgcaaaggc tgtgcagaaa agtctgacta catccggaag    420
ataaatgaac tgatgcctaa atatgccccc aaggcagcca gtgcaccgac cgatttgtag    480
```

<210> SEQ ID NO 11
<211> LENGTH: 43
<212> TYPE: PRT

<213> ORGANISM: Homo sapiens

<400> SEQUENCE: 11

Leu Arg Pro Gly Asp Cys Glu Val Cys Ile Ser Tyr Leu Gly Arg Phe
1               5                   10                  15

Tyr Gln Asp Leu Lys Asp Arg Asp Val Thr Phe Ser Pro Ala Thr Ile
                20                  25                  30

Glu Asn Glu Leu Ile Lys Phe Cys Arg Glu Ala
            35                  40

<210> SEQ ID NO 12
<211> LENGTH: 52
<212> TYPE: PRT
<213> ORGANISM: Homo sapiens

<400> SEQUENCE: 12

Arg Gly Lys Glu Asn Arg Leu Cys Tyr Tyr Ile Gly Ala Thr Asp Asp
1               5                   10                  15

Ala Ala Thr Lys Ile Ile Asn Glu Val Ser Lys Pro Leu Ala His His
                20                  25                  30

Ile Pro Val Glu Lys Ile Cys Glu Lys Leu Lys Lys Asp Ser Gln
            35                  40                  45

Ile Cys Glu Leu
    50

<210> SEQ ID NO 13
<211> LENGTH: 52
<212> TYPE: PRT
<213> ORGANISM: Homo sapiens

<400> SEQUENCE: 13

Lys Tyr Asp Lys Gln Ile Asp Leu Ser Thr Val Asp Leu Lys Lys Leu
1               5                   10                  15

Arg Val Lys Glu Leu Lys Lys Ile Leu Asp Asp Trp Gly Glu Thr Cys
                20                  25                  30

Lys Gly Cys Ala Glu Lys Ser Asp Tyr Ile Arg Lys Ile Asn Glu Leu
            35                  40                  45

Met Pro Lys Tyr
    50

<210> SEQ ID NO 14
<211> LENGTH: 179
<212> TYPE: PRT
<213> ORGANISM: Bos taurus

<400> SEQUENCE: 14

Met Trp Ala Thr His Gly Leu Ala Val Ala Leu Ala Leu Ser Val Leu
1               5                   10                  15

Pro Ala Ser Arg Ala Leu Arg Gln Gly Asp Cys Glu Val Cys Ile Ser
                20                  25                  30

Tyr Leu Gly Arg Phe Tyr Gln Asp Leu Lys Asp Arg Asp Val Thr Phe
            35                  40                  45

Ser Pro Ala Ser Ile Glu Lys Glu Leu Ile Lys Phe Cys Arg Glu Ala
        50                  55                  60

Arg Gly Lys Glu Asn Arg Leu Cys Tyr Tyr Ile Gly Ala Thr Glu Asp
65                  70                  75                  80

Ala Ala Thr Lys Ile Ile Asn Glu Val Ser Lys Pro Leu Ser His His
                85                  90                  95

```
Ile Pro Val Glu Lys Ile Cys Glu Lys Leu Lys Lys Asp Ser Gln
            100                 105                 110
Ile Cys Glu Leu Lys Tyr Asp Lys Gln Ile Asp Leu Ser Thr Val Asp
        115                 120                 125
Leu Lys Lys Leu Arg Val Lys Glu Leu Lys Lys Ile Leu Asp Asp Trp
    130                 135                 140
Gly Glu Thr Cys Lys Gly Cys Ala Glu Lys Ser Asp Tyr Ile Arg Lys
145                 150                 155                 160
Ile Asn Glu Leu Met Pro Lys Tyr Ala Pro Lys Ala Ala Ser Ser Arg
                165                 170                 175
Thr Asp Leu

<210> SEQ ID NO 15
<211> LENGTH: 179
<212> TYPE: PRT
<213> ORGANISM: Sus scrofa
<220> FEATURE:
<221> NAME/KEY: VARIANT
<222> LOCATION: 149, 167
<223> OTHER INFORMATION: Xaa = Any Amino Acid

<400> SEQUENCE: 15

Met Trp Phe Thr His Gly Leu Ala Val Ala Leu Ala Leu Ser Val Leu
1               5                   10                  15
Pro Ala Ser Arg Ala Leu Arg Pro Gly Asp Cys Glu Val Cys Ile Ser
            20                  25                  30
Tyr Leu Gly Arg Phe Tyr Gln Asp Leu Lys Asp Arg Asp Val Thr Phe
        35                  40                  45
Ser Pro Ala Ser Ile Glu Lys Glu Leu Thr Lys Phe Cys Arg Glu Ala
    50                  55                  60
Arg Gly Lys Glu Asn Arg Leu Cys Tyr Tyr Ile Gly Ala Thr Asp Asp
65                  70                  75                  80
Ala Ala Thr Lys Ile Ile Asn Glu Val Ser Lys Pro Leu Ala His His
                85                  90                  95
Ile Pro Val Glu Lys Ile Cys Glu Lys Leu Met Lys Lys Asp Ser Gln
            100                 105                 110
Ile Cys Glu Leu Lys Tyr Asp Lys Gln Ile Asp Leu Ser Thr Val Asp
        115                 120                 125
Leu Lys Lys Leu Arg Val Lys Glu Leu Lys Lys Ile Leu Asp Asp Trp
    130                 135                 140
Gly Glu Thr Cys Xaa Gly Cys Ala Glu Lys Ser Asp Tyr Ile Arg Lys
145                 150                 155                 160
Ile Asn Glu Leu Met Pro Xaa Tyr Ala Pro Lys Ala Ala Ser Ser Arg
                165                 170                 175
Thr Asp Leu

<210> SEQ ID NO 16
<211> LENGTH: 10
<212> TYPE: PRT
<213> ORGANISM: Rattus norvegicus

<400> SEQUENCE: 16

Asp Val Thr Phe Ser Pro Ala Thr Ile Glu
1               5                   10

<210> SEQ ID NO 17
<211> LENGTH: 9
<212> TYPE: PRT
```

```
<213> ORGANISM: Rattus norvegicus

<400> SEQUENCE: 17

Gln Ile Asp Leu Ser Thr Val Asp Leu
1               5
```

DOPAMINERGIC NEURONAL SURVIVAL-PROMOTING FACTORS AND USES THEREOF

CROSS-REFERENCE

This application is a continuation application of U.S. application Ser. No. 12/535,029, filed Aug. 4, 2009, now U.S. Pat. No. 8,084,425, which is a continuation of U.S. application Ser. No. 10/102,265, filed Mar. 20, 2002, now abandoned, which claims benefit of and priority to provisional U.S. Application No. 60/277,516, filed Mar. 20, 2001, each of which is incorporated herein by reference in their entirety and to which applications we claim priority under 35 USC §§119, 120.

BACKGROUND OF THE INVENTION

The invention relates to compositions and methods for increasing the survival of neurons.

The growth, survival, and differentiation of neurons in the peripheral and central nervous systems (PNS and CNS, respectively) are dependent, in part, on target-derived, paracrine, and autocrine neurotrophic factors. Conversely, the lack of neurotrophic factors is thought to play a role in the etiology of neurodegenerative diseases such as Parkinson's disease, Alzheimer's disease, and amyotrophic lateral sclerosis (ALS or Lou Gehrig's disease). In neuronal cell cultures, neurotrophic support is provided by co-culturing with astrocytes or by providing conditioned medium (CM) prepared from astrocytes. Astrocytes of ventral mesencephalic origin exert much greater efficacy in promoting the survival of ventral, mesencephalic dopaminergic neurons, compared with astrocytes from other regions of the CNS, such as the neostriatum and cerebral cortex. In chronic, mesencephalic cultures of 21 days in vitro (DIV) or longer, the percentage of dopaminergic neurons increases from 20% to 60%, coincident with proliferation of a monolayer of astrocytes. In contrast, in conditions in which the proliferation of astrocytes was inhibited, dopaminergic, but not GABAergic neurons, were almost eliminated from the cultures by 5 DIV. These results demonstrate the importance of homotypically-derived astrocytes for the survival and development of adjacent dopaminergic neurons, and suggest that mesencephalic astrocytes are a likely source of a physiological, paracrine neurotrophic factor for mesencephalic dopaminergic neurons.

The repeated demonstration that astrocytes secrete molecules that promote neuronal survival has made astrocytes a focus in the search for therapeutics to treat neurodegenerative diseases. Many laboratories have attempted to isolate astrocyte-derived neurotrophic factors, but have been hindered by a major technical problem: serum is an essential component of the medium for the optimal growth of primary astrocytes in culture, yet the presence of serum interferes with the subsequent purification of factors secreted into the conditioned medium.

Thus, there is a need to identify and purify new neurotrophic factors and to identify new methods to produce conditioned medium that are compatible with protein isolation techniques.

SUMMARY OF THE INVENTION

We previously isolated a spontaneously immortalized type-1 astrocyte-like cell line, referred to as ventral mesencephalic cell line-1 (VMCL-1). This cell line, deposited with the American Type Culture Collection (ATCC; Manassas, Va.; ATCC Accession No: PTA-2479; deposit date: Sep. 18, 2000), was derived from the ventral mesencephalon and retained the characteristics of primary, type-1 astrocytes, but grows robustly in a serum-free medium. The CM prepared from these cells contains one or more neuronal survival factors that increase the survival of mesencephalic dopaminergic neurons at least 3-fold, and promotes their development as well.

Using a multi-step purification process, we have identified arginine-rich protein (ARP) as a protein that co-purifies with the dopaminergic neuronal survival-promoting activity of VMCL-1 CM. As the protein and the activity co-purified through five purification steps, we conclude that this protein is one of the factors in the VMCL-1 CM having the desired dopaminergic neuronal survival-promoting activity.

We have also discovered that ARP is produced in a previously unrecognized secreted form; we refer to this form as MANF (mature astrocyte-derived neurotrophic factor), MANF lacks the N-terminal arginine-rich portion of the protein, as is shown in FIG. 2 and SEQ ID NO: 3. Based on examination of the sequences, we believe that this secreted form results from the cleavage of a previously unidentified splice variant of ARP (ARPβ or pro-MANF), which has the sequence shown in SEQ ID NO: 2. MANF, and biologically active analogs, derivatives, and fragments thereof, are collectively referred to as "MANIF polypeptides."

Accordingly, in a first aspect, the invention features a substantially purified MANF polypeptide. In one embodiment, the MANF polypeptide has the amino acid sequence of SEQ ID NO: 2, 3, 4, 5, 6, or 7. In another embodiment, the MANF polypeptide includes one or more conservative amino acid substitutions relative to the amino acid sequence of SEQ ID NO: 2, 3, 4, 5, 6, or 7, or is otherwise substantially identical to a protein having one of these amino acid sequences.

In a second aspect, the invention features a substantially purified polynucleotide encoding a MANF polypeptide. As described above, the MANF polypeptide may have the amino acid sequence of SEQ ID NO: 2, 3, 4, 5, 6, or 7, or may have one or more conservative amino acid substitutions relative to these amino acid sequences. In one embodiment, the polynucleotide encodes a protein substantially identical to a protein having the amino acid sequence of SEQ ID NO: 2, 3, 4, 5, 6, or 7. In another embodiment, the polynucleotide consists of the sequence of SEQ ID NO: 9 or 10.

In a third aspect, the invention features an expression vector that includes the polynucleotide of the second aspect. The expression vector can be, for example, an adenoviral vector or a retroviral vector. In one particular embodiment, the polynucleotide is operably linked to regulatory sequences that allow for the expression of the polynucleotide in a neural cell.

In a fourth aspect, the invention features a pharmaceutical composition that includes: (i) a substantially purified MANF polypeptide; and (ii) a carrier that is pharmaceutically acceptable for administration to the central nervous system.

In a fifth aspect, the invention features a pharmaceutical composition that includes: (i) a substantially purified MANF polypeptide; (ii) a pharmaceutically acceptable carrier; and (iii) a neural cell. The neural cell can be, for example, a neuron, a neural stem cell, or a neuronal precursor cell.

In a sixth aspect, the invention features a method for increasing survival of dopaminergic neurons, the method including the step of contacting the dopaminergic neurons with a survival-promoting amount of a substantially purified MANF polypeptide.

In a seventh aspect, the invention features a method for growing dopaminergic neurons for transplantation. This method includes the step of culturing the neurons, or progenitor cells thereof, with a survival-promoting amount of a substantially purified MANF polypeptide. In one embodiment, the MANF polypeptide is administered with a pharmaceutically acceptable excipient.

In an eighth aspect, the invention features a method of treating a patient having a disease or disorder of the nervous system. The method including the step of administering to the patient a dopaminergic neuronal survival-promoting amount of a substantially purified MANF polypeptide.

In a ninth aspect, the invention features a method for preventing dopaminergic neuronal cell death in a mammal. This method includes the step of administering to the mammal a dopaminergic neuronal survival-promoting amount of a substantially purified MANF polypeptide.

In a tenth aspect method of transplanting cells into the nervous system of a mammal such as a human, including (i) transplanting cells into the nervous system of the mammal; and (ii) administering a dopaminergic neuronal survival-promoting amount of a MANF polypeptide to the mammal in a time window from two to four hours before transplanting the cells to two to four hours after transplanting the cells.

In an eleventh aspect, the invention features another method of transplanting cells into the nervous system of a mammal such as a human. This method includes the steps of: (a) contacting the cells with a MANF polypeptide; and (b) transplanting the cells of step (a) into the nervous system of the mammal. It is desirable that step (a) and step (b) be performed within four hours of each other.

In particular embodiments of the fourth, fifth, sixth, seventh, eighth, ninth, tenth, or eleventh aspect, the MANF polypeptide consists of the sequence of SEQ ID NO: 2, 3, 4, 5, 6, or 7, or consists essentially of SEQ ID NO: 2, 3, 4, 5, 6, or 7

As demonstrated herein, dopaminergic neurons are, in large part, prevented from dying in the presence of a MANF polypeptide. Dopaminergic neurons of the mesencephalon die in patients having Parkinson's disease. The invention thus provides a treatment of Parkinson's disease. In addition, the use of a MANF polypeptide in the treatment of disorders or diseases of the nervous system in which the loss of dopaminergic neurons is present or anticipated is included in the invention.

The discovery that MANF is involved in dopaminergic neuronal survival allows MANF to be used in a variety of diagnostic tests and assays for identification of dopaminergic neuronal survival-promoting drugs. MANF expression can also serve as a diagnostic tool for determining whether a person is at risk for a neurodegenerative disorder. This diagnostic process can lead to the tailoring of drug treatments according to patient genotype (referred to as pharmacogenomics), including prediction of the patient's response (e.g., increased or decreased efficacy or undesired side effects upon administration of a compound or drug).

Antibodies to a MANF polypeptide can be used both as therapeutics and diagnostics. Antibodies are produced by immunologically challenging a B-cell-containing biological system, e.g., an animal such as a mouse, with a MANF polypeptide to stimulate production of anti-MANF by the B-cells, followed by isolation of the antibody from the biological system. Such antibodies can be used to measure MANF polypeptide in a biological sample such as serum, by contacting the sample with the antibody and then measuring immune complexes as a measure of the MANF polypeptide in the sample. Antibodies to MANF can also be used as therapeutics for the modulation of MANF biological activity.

Thus, in another aspect, the invention features a purified antibody that specifically binds to a MANF polypeptide.

In yet another aspect, the invention features a method for determining whether a candidate compound modulates MANF-mediated dopaminergic neuronal survival-promoting activity, including: (a) providing a MANF polypeptide; (b) contacting the MANF polypeptide with the candidate compound; and (c) measuring MANF biological activity, wherein altered MANF biological activity, relative to that of a MANF polypeptide not contacted with the compound, indicates that the candidate compound modulates MANF biological activity. The MANF polypeptide can be in a cell or in a cell-free assay system.

In another aspect, the invention features a method for determining whether candidate compound is useful for decreasing neurodegeneration, the method including the steps of: (a) providing a MANF polypeptide; (b) contacting the polypeptide with the candidate compound; and (c) measuring binding of the MANF polypeptide, wherein binding of the MANF polypeptide indicates that the candidate compound is useful for decreasing neurodegeneration.

In particular embodiments of the foregoing screening methods of the present invention, the cell is in an animal and the MANF polypeptide consists of the sequence of SEQ ID NO: 2, 3, 4, 5, 6, or 7, or consists essentially of SEQ ID NO: 2, 3, 4, 5, 6, or 7.

The invention also features screening methods for identifying factors that potentiate or mimic MANF biological activity. In these screening methods for potentiators, the ability of candidate compounds to increase MANF expression, stability, or biological activity is tested using standard techniques. A candidate compound that binds to MANF may act as a potentiating agent. A mimetic (e.g., a compound that binds a MANF receptor) is a compound capable of acting in the absence of a MANF polypeptide.

By "substantially purified" is meant that a polypeptide (e.g., a MANF polypeptide) has been separated from the components that naturally accompany it. Typically, the polypeptide is substantially purified when it is at least 60%, by weight, free from the proteins and naturally-occurring organic molecules with which it is naturally associated. Preferably, the polypeptide is at least 75%, more preferably at least 90%, and most preferably at least 99%, by weight, pure. A substantially purified polypeptide may be obtained, for example, by extraction from a natural source (e.g., a neural cell), by expression of a recombinant nucleic acid encoding the polypeptide, or by chemically synthesizing the protein. Purity can be measured by any appropriate method, e.g., by column chromatography, polyacrylamide gel electrophoresis, or HPLC analysis.

A polypeptide is substantially free of naturally associated components when it is separated from those contaminants that accompany it in its natural state. Thus, a polypeptide which is chemically synthesized or produced in a cellular system different from the cell from which it naturally originates will be substantially free from its naturally associated components. Accordingly, substantially purified polypeptides include those which naturally occur in eukaryotic organisms but are synthesized in *E. Coli* or other prokaryotes.

By "polypeptide" or "protein" is meant any chain of more than two amino acids, regardless of post-translational modification such as glycosylation or phosphorylation.

A MANF polypeptide that is part of the invention is one having dopaminergic neuronal survival-promoting activity ("MANF biological activity") and encoded by a nucleic acid that either hybridizes at high stringency to a cDNA encoding human MANF (SEQ ID NO: 2, 3, or 4) or is substantially identical to human MANF. Included in this definition are pro-MANF polypeptide (e.g., human pro-MANF; SEQ ID NO: 2), synthetic human MANF (SEQ ID NO: 4), peptide domains of human MANF (e.g., LRPGDCEVCISYLGR-FYQDLKDRDV TFSPATIENELIKFCREA; SEQ ID NO: 11; RGKENRLCYYIGATDDAATKIIN EVSKPLAH-HIPVEKICEKLKKKDSQICEL; SEQ ID NO: 12 and KYD-KQIDLS TVDLKKLRVKELKKILDDWGETCKGCAE-KSDYIRKINELMPKY; SEQ ID NO: 13) predicted to have MANF biological activity, and counterpart MANF polypeptides from species such as mouse (e.g., SEQ ID NO: 5, 6, and 7), cow (FIG. 11A; SEQ ID NO: 14), and pig (FIG. 11B; SEQ ID NO: 15). Specifically excluded from the definition of MANF polypeptides are ARP proteins that contain the arginine-rich amino terminus (e.g., amino acids 1 to 55 of SEQ ID NO: 1). Thus, human ARP (SEQ ID NO: 1) is not considered a MANF polypeptide.

A polynucleotide that is a part of the invention is one encoding a MANF polypeptide, as defined above. Exemplary polynucleotides are represented, for example, by the sequences of SEQ ID NO: 9 and SEQ ID NO: 10.

By "substantially identical" is meant a polypeptide or polynucleotide exhibiting at least 5%, preferably 90%, more preferably 95%, and most preferably 97% identity to a reference amino acid or nucleic acid sequence. For polypeptides, the length of comparison sequences will generally be at least 16 amino acids, preferably at least 20 amino acids, more preferably at least 25 amino acids, and most preferably 35 amino acids. For polynucleotides, the length of comparison sequences will generally be at least 50 nucleotides, preferably at least 60 nucleotides, more preferably at least 75 nucleotides, and most preferably 110 nucleotides.

Sequence identity is typically measured using sequence analysis software with the default parameters specified therein (e.g., Sequence Analysis Software Package of the Genetics Computer Group, University of Wisconsin Biotechnology Center, 1710 University Avenue, Madison, Wis. 53705). This software program matches similar sequences by assigning degrees of homology to various substitutions, deletions, and other modifications. Conservative substitutions typically include substitutions within the following groups: glycine, alanine, valine, isoleucine, leucine; aspartic acid, glutamic acid, asparagine, glutamine; serine, threonine; lysine, arginine; and phenylalanine, tyrosine.

By "high stringency conditions" is meant hybridization in 2×SSC at 40° C. with a DNA probe length of at least 40 nucleotides. For other definitions of high stringency conditions, see F. Ausubel et al., *Current Protocols in Molecular Biology*, pp. 6.3.1-6.3.6, John Wiley & Sons, New York, N.Y., 1994, hereby incorporated by reference.

By "compound" or "factor" is meant a molecule having an activity that promotes the survival (or, conversely, prevents the death) of dopaminergic neurons in a standard cell survival assay.

By "composition" is meant a collection of polypeptides, including a polypeptide of the present invention.

By "pharmaceutically acceptable excipient" is meant an excipient, carrier, or diluent that is physiologically acceptable to the treated mammal while retaining the therapeutic properties of the polypeptide with which it is administered. One exemplary pharmaceutically acceptable carrier is physiological saline solution. Other physiologically acceptable carriers and their formulations are known to one skilled in the art and described, for example, in *Remington: The Science and Practice of Pharmacy*, (20th ed.) ed. A. R. Gennaro A R., 2000, Lippencott Williams & Wilkins.

By a compound having "dopaminergic neuronal survival-promoting activity" is the presence of the compound increases survival of dopaminergic neurons by at least two-fold in a dopaminergic neuronal survival assay (such as the one described herein) relative to survival of dopaminergic neurons in the absence of the compound. The increase in the survival of dopaminergic neurons can be by at least three-fold, more preferably by at least four-fold, and most preferably by at least five-fold. The assay can be an in vitro assay or an in vivo assay.

The present invention provides new methods and reagents for the prevention of neuronal cell death. The invention also provides pharmaceutical compositions for the treatment of neurological diseases or disorders of which aberrant neuronal cell death is one of the causes.

Other features and advantages of the invention will be apparent from the following description of the preferred embodiments thereof.

BRIEF DESCRIPTION OF THE DRAWINGS

FIG. 2 is a schematic illustration showing human ARP (SEQ ID NO: 1), human pro-MANF (SEQ ID NO: 2) human MANF (SEQ ID NO: 3), and a synthetic human MANF lacking the signal sequence (SEQ ID NO: 4).

FIG. 3 is a schematic illustration showing mouse pro-MANF (SEQ ID NO: 5), mouse MANF (SEQ ID NO: 6), and a synthetic mouse MANF lacking the signal sequence (SEQ ID NO: 7

FIG. 4 is a schematic illustration showing the sequence of polynucleotides encoding human ARP (SEQ ID NO: 8), human pro-MANF (SEQ ID NO: 9), and human MANF (SEQ ID NO: 10).

FIGS. 11A and 11B are schematic illustrations showing the sequence of cow (FIG. 11A) and pig (FIG. 11B) pro-MANF. The signal peptide is indicated in bold.

DETAILED DESCRIPTION OF THE INVENTION

Figure 1:
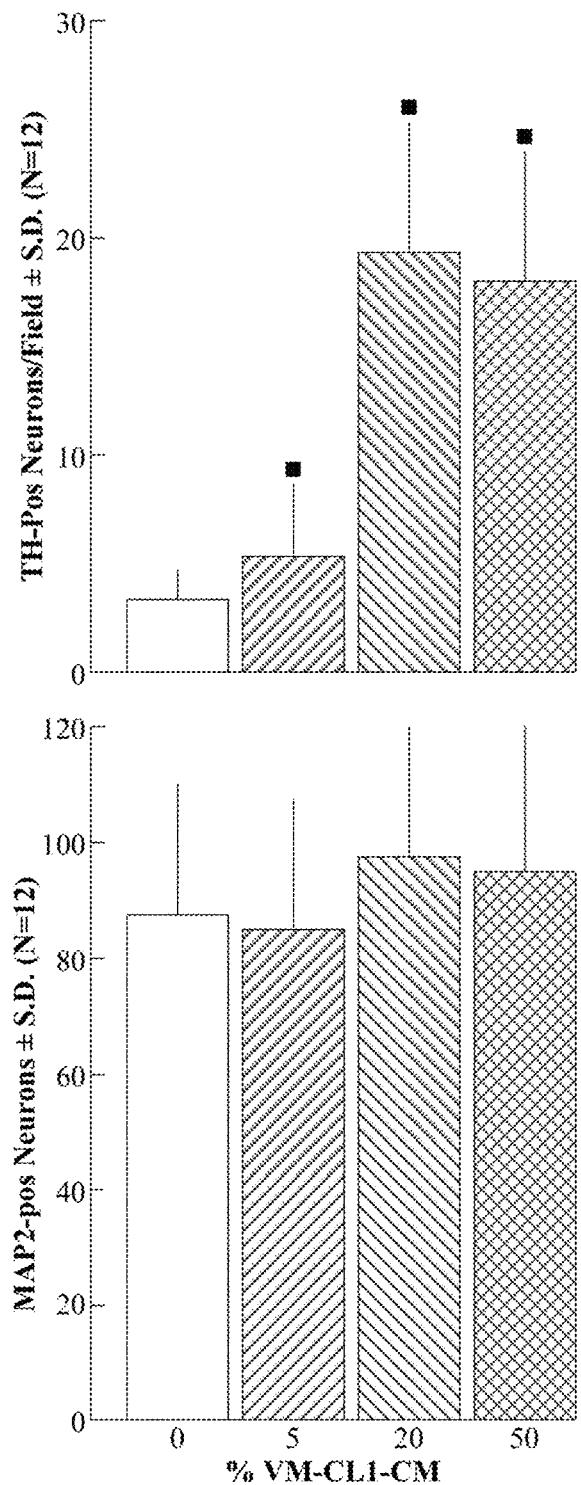
FIG. 1 is a schematic illustration showing the effect of different amounts of conditioned medium from VMCL-1 cell cultures on the survival of tyrosine hydroxylase-positive cells (top panel) and MAP2-positive cells (bottom panel).

We previously discovered that a cell line of mesencephalic origin (termed "VMCL-1") secretes a factor that, in turn, promotes differentiation and survival of dopaminergic neurons. This cell line grows robustly in a serum-free medium. Moreover, the CM prepared from these cells contains one or more dopaminergic neuronal survival factors that increase the survival of mesencephalic dopaminergic neurons at least 3-fold, and promotes their development as well.

We purified, from the VMCL-1 cell line, a protein that we identified to be ARP. We purified this protein as follows. A 3 L volume of VMCL-1 conditioned medium was prepared, and subjected to five sequential steps of column chromatography. At each purification step, each column fraction was tested for biological activity in the bioassay referred to above. An estimate of the effect of each fraction on dopaminergic neuronal survival was done at 24 hour intervals, over a period of five days, and rated on a scale of 1-10. After the fifth purification step, the biologically active fraction and an adjacent inactive fraction were analyzed by SDS-PAGE. The results of the SDS-PAGE analysis revealed a distinctive protein band in the 20 kDa range in the lane from the active fraction. The "active" band was excised and subjected to tryptic digest, and the molecular mass and sequence of each peptide above background were determined by mass spectrometry analysis. The following two peptide sequences were identified: DVTFSPATIE (SEQ ID NO: 6) and QIDLSTVDL (SEQ ID NO: 7). A search of the database identified a match for human arginine-rich protein and its mouse orthologue. The predicted protein encoded by the mouse EST sequence is about 95% identical to the predicted human protein. A search of the rat EST database revealed two sequences, one (dbEST Id: 4408547; EST name: EST348489) having significant homology at the amino acid level to the human and mouse proteins. The full-length rat sequence was not in the GenBank database. Additionally, we discovered that the sequence of the human ARP in GenBank was incorrect. The correct sequence is depicted in SEQ ID NO: 1.

We have discovered that human ARP is cleaved such that the arginine-rich amino-terminus is separated from the carboxy-terminus to produce human pro-MANF (SEQ ID NO: 2). The cleaved carboxy-terminal fragment contains a signal peptide, resulting in the secretion of human MANF (SEQ ID NO: 3) from the cell.

Both the secreted form and the unsecreted form of MANF (collectively referred to as MANF polypeptides) have neurotrophic activity and are useful as neurotrophic factor for the treatment of a neurodegenerative disease such as Parkinson's Disease and for improving dopaminergic neuronal survival during or following transplantation into a human. MANF polypeptides can also be used to improve the in vitro production of neurons for transplantation. In another use, MANF polypeptides can be used for the identification of compounds that modulate or mimic MANF's dopaminergic neuronal survival-promoting activity. MANF polypeptides can also be used to identify MANF receptors. Each of these uses is described in greater detail below.

Identification of Molecules that Modulate MANF Biological Activity

The effect of candidate molecules on MANF-mediated regulation of dopaminergic neuronal survival may be measured at the level of translation by using standard protein detection techniques, such as western blotting or immunoprecipitation with a MANF-specific antibody.

Compounds that modulate the level of MANF may be purified, or substantially purified, or may be one component of a mixture of compounds such as an extract or supernatant obtained from cells (Ausubel et al., supra). In an assay of a mixture of compounds, MANF expression is measured in cells administered progressively smaller subsets of the compound pool (e.g., produced by standard purification techniques such as HPLC or FPLC) until a single compound or minimal number of effective compounds is demonstrated to modulate MANF expression.

Compounds may also be directly screened for their ability to modulate MANF-mediated dopaminergic neuronal survival. In this approach, the amount of dopaminergic neuronal survival in the presence of a candidate compound is compared to the amount of dopaminergic neuronal survival in its absence, under equivalent conditions. Again, the screen may begin with a pool of candidate compounds, from which one or more useful modulator compounds are isolated in a step-wise fashion. Survival-promoting activity may be measured by any standard assay.

Another method for detecting compounds that modulate the activity of MANF is to screen for compounds that interact physically with MANF. These compounds may be detected by adapting interaction trap expression systems known in the art. These systems detect protein interactions using a transcriptional activation assay and are generally described by Gyuris et al. (Cell 75:791-803, 1993) and Field et al., (Nature 340:245-246, 1989). Alternatively, MANF or a biologically active fragment thereof can be labeled with $^{125}$I Bolton-Hunter reagent (Bolton et al. Biochem. J. 133: 529, 1973). Candidate molecules previously arrayed in the wells of a multi-well plate are incubated with the labeled MANF, then washed; any wells with labeled MANF complex are assayed. Data obtained using different concentrations of MANF can be used to calculate values for the number, affinity, and association of MANF with the candidate molecules.

Compounds or molecules that function as modulators of MANF dopaminergic neuronal survival-promoting activity may include peptide and non-peptide molecules such as those present in cell extracts, mammalian serum, or growth medium in which mammalian cells have been cultured.

A molecule that modulates MANF expression or MANF-mediated biological activity such that there is an increase in neuronal cell survival is considered useful in the invention; such a molecule may be used, for example, as a therapeutic agent, as described below.

The discovery of MANF as a neurotrophic factor that promotes the survival of dopaminergic neurons allows for its use for the therapeutic treatment of neurodegenerative diseases such as Parkinson's disease.

To add a MANF polypeptide to cells in order to prevent neuronal death, it is preferable to obtain sufficient amounts of a recombinant MANF polypeptide from cultured cell systems that can express the protein. A preferred MANF polypeptide is human MANF, but MANF polypeptides derived from other animals (e.g., pig, rat, mouse, dog, baboon, cow, and the like) can also be used. Delivery of the protein to the affected tissue can then be accomplished using appropriate packaging or administrating systems. Alternatively, small molecule analogs may be used and administered to act as MANF agonists and in this manner produce a desired physiological effect.

Gene therapy is another potential therapeutic approach in which normal copies of the gene encoding a MANF polypeptide (or a polynucleotide encoding MANF sense RNA) is introduced into cells to successfully produce the MANF polypeptide. The gene must be delivered to those cells in a form in which it can be taken up and encode for sufficient protein to provide effective dopaminergic neuronal survival-promoting activity.

Retroviral vectors, adenoviral vectors, adenovirus-associated viral vectors, or other viral vectors with the appropriate tropism for neural cells may be used as a gene transfer delivery system for a therapeutic MANF construct. Numerous vectors useful for this purpose are generally known (Miller, Human Gene Therapy 15-14, 1990; Friedman, Science 244: 1275-1281, 1989; Eglitis and Anderson, BioTechniques 6:608-614, 1988; Tolstoshev and Anderson, Curr. Opin. Biotech. 1:55-61, 1990; Sharp, The Lancet 337: 1277-1278, 1991; Cometta et al., Nucl. Acid Res. and Mol. Biol. 36: 311-322, 1987; Anderson, Science 226: 401-409, 1984; Moen, Blood Cells 17: 407-416, 1991; Miller et al., Biotech. 7: 980-990, 1989; Le Gal La Salle et al., Science 259: 988-990, 1993; and Johnson, Chest 107: 77S-83S, 1995). Retroviral vectors are particularly well developed and have been used in clinical settings (Rosenberg et al., N. Engl. J. Med. 323: 370, 1990; Anderson et al., U.S. Pat. No. 5,399,346). Non-viral approaches may also be employed for the introduction of therapeutic DNA into the desired cells. For example, a MANF-encoding polynucleotide may be introduced into a cell by lipofection (Feigner et al., Proc. Natl. Acad. Sci. USA 84: 7413, 1987; Ono et al., Neurosci. Lett. 117: 259, 1990; Brigham et al., Am. J. Med. Sci. 298:278, 1989; Staubinger et al., Meth. Enzymol. 101:512, 1983), asialorosonucoid-polylysine conjugation (Wu et al., J. Biol. Chem. 263:14621, 1988; Wu et al., J. Biol. Chem. 264:16985, 1989); or, less preferably, micro-injection under surgical conditions (Wolff et al., Science 247:1465, 1990).

Gene transfer could also be achieved using non-viral means requiring infection in vitro. This would include calcium phosphate, DEAE dextran, electroporation, and protoplast fusion. Liposomes may also be potentially beneficial for delivery of DNA into a cell. Although these methods are available, many of these are of lower efficiency.

In the constructs described, MANF or pro-MANF cDNA expression can be directed from any suitable promoter (e.g., the human cytomegalovirus (CMV), simian virus 40 (SV40), or metallothionein promoters), and regulated by any appropriate mammalian regulatory element. For example, if desired, enhancers known to preferentially direct gene expression in neural cells may be used to direct MANF polypeptide expression. The enhancers used could include, without limitation, those that are characterized as tissue- or cell-specific in their expression.

RNA molecules may be modified to increase intracellular stability and half-life. Possible modifications include, but are not limited to, the addition of flanking sequences at the 5' and/or 3' ends of the molecule or the use of phosphorothioate or 2' O-methyl rather than phosphodiesterase linkages within the backbone of the molecule. This concept can be extended in all of these molecules by the inclusion of nontraditional bases such as inosine, queosine, and wybutosine, as well as acetyl-, methyl-, thio-, and similarly modified forms of adenine, cytidine, guanine, thymine, and uridine which are not as easily recognized by endogenous endonucleases.

Another therapeutic approach within the invention involves administration of a recombinant MANF polypeptide, either directly to the site of a potential or actual cell loss (for example, by injection) or systemically (for example, by any conventional recombinant protein administration technique).

An additional embodiment of the invention relates to the administration of a pharmaceutical composition, in conjunction with a pharmaceutically acceptable carrier, for any of the therapeutic effects discussed above. Such pharmaceutical compositions may consist of AMNF polypeptides, antibodies to MANF polypeptides, and/or mimetics and agonists of MANF polypeptides. The compositions may be administered alone or in combination with at least one other agent, such as a stabilizing compound, which may be administered in any sterile, biocompatible pharmaceutical carrier, including, but not limited to, saline, buffered saline, dextrose, and water.

The compositions may be administered to a patient alone, or in combination with other agents, drugs or hormones.

In one example, a MANF polypeptide is administered to a subject at the site that cells are transplanted. The administration of the MANF polypeptide can be performed before, during, or after the transplantation of the cells. Preferably, the two steps are within about four hours of each other. If desirable, the MANF polypeptide can be repeatedly administered to the subject at various intervals before and/or after cell transplantation. This protective administration of the MANF polypeptide may occur months or even years after the cell transplantation.

In addition to its administration to a human or other mammal, a MANF polypeptide can also be used in culture to improve the survival of neurons during their production any time prior to transplantation. In one example, the cells to be transplanted are suspended in a pharmaceutical carrier that also includes a survival-promoting amount of a MANF polypeptide. A MANF polypeptide can also be administered to the cultures earlier in the process (e.g., as the neurons are first differentiating). It is understood that the neurons need not be primary dopaminergic neurons. Neurons (e.g., dopaminergic neurons) that are differentiated, either in vitro or in vivo, from stem cells or any other cell capable of producing neurons can be cultured in the presence of a MANF polypeptide during their production and maintenance.

Parenteral formulations may be in the form of liquid solutions or suspensions; for oral administration, formulations may be in the form of tablets or capsules; and for intranasal formulations, in the form of powders, nasal drops, or aerosols.

Methods well known in the art for making formulations are to be found in, for example, *Remington: The Science and Practice of Pharmacy*, (20th ed.) ed. A. R. Gennaro Ark., 2000, Lippencott Williams & Wilkins. Formulations for parenteral administration may, for example, contain as excipients sterile water or saline, polyalkylene glycols such as polyethylene glycol, oils of vegetable origin, or hydrogenated naphthalenes, biocompatible, biodegradable lactide polymer, or polyoxyethylene-polyoxypropylene copolymers may be used to control the release of the present factors. Other potentially useful parenteral delivery systems for the factors include ethylene-vinyl acetate copolymer particles, osmotic pumps, implantable infusion systems, and liposomes. Formulations for inhalation may contain as excipients, for example, lactose, or may be aqueous solutions containing, for example, polyoxyethylene-9-lauryl ether, glycocholate and deoxycholate, or may be oily solutions for administration in the form of nasal drops, or as a gel to be applied intranasally.

The present factors can be used as the sole active agents, or can be used in combination with other active ingredients, e.g., other growth factors which could facilitate dopaminergic neuronal survival in neurological diseases, or peptidase or protease inhibitors.

The concentration of the present factors in the formulations of the invention will vary depending upon a number of issues, including the dosage to be administered, and the route of administration.

In general terms, the factors of this invention may be provided in an aqueous physiological buffer solution containing about 0.1 to 10% w/v polypeptide for parenteral administration. General dose ranges are from about 1 mg/kg to about 1 g/kg of body weight per day; a preferred dose range is from about 0.01 mg/kg to 100 mg/kg of body weight per day. The preferred dosage to be administered is likely to depend upon the type and extent of progression of the pathophysiological condition being addressed, the overall health of the patient, the make up of the formulation, and the route of administration.

While human MANF is preferred for use in the methods described herein, MANF has been identified in numerous species, including rat, mouse, and cow. One in the art will recognize that the identification of MANF from other animals can be readily performed using standard methods. Any protein having dopaminergic neuronal survival-promoting activity and encoded by a nucleic acid that hybridizes to the cDNA encoding human ARP is considered part of the invention.

The following examples are to illustrate the invention. They are not meant to limit the invention in any way.

EXAMPLE 1

Production and Analysis of VMCL-1 Cells

The VMCL-1 cell line was made as follows. Rat E14 mesencephalic cells, approximately 2-3% of which are glioblasts, were incubated in medium containing 10% (v/v) fetal bovine serum for 12 hours and subsequently expanded in a serum-free medium, containing basic fibroblast growth factor (bFGF) as a mitogen. After more than 15 DIV, several islets of proliferating, glial-like cells were observed. Following isolation and passaging, the cells (referred to herein as VMCL-1 cells) proliferated rapidly in either a serum-free or serum-containing growth medium. Subsequent immunocytochemical analysis showed that they stained positive for two astrocytic markers, GFAP and vimentin, and negative for markers of oligodendroglial or neuronal lineages, including A2B5, O4, GalC and MAP2. We have deposited the VMCL-1 cell line with the ATCC (Accession No: PTA-2479; deposit date: Sep. 18, 2000).

Serum-free CM, prepared from the VMCL-1 cells, caused increased survival and differentiation of E14 mesencephalic dopaminergic neurons in culture. These actions are similar to those exerted by CM derived from primary, mesencephalic type-1 astrocytes. The expression of mesencephalic region-specific genes (e.g., wnt-1, en-1, en-2, pax-2, pax-5 and pax-8), was similar between VMCL-1 cells and primary, type-1 astrocytes of E14 ventral mesencephalic origin. In both, wnt-1 was expressed strongly, and en-1 less strongly, supporting an expression pattern expected of their mesencephalic origin. A chromosomal analysis showed that 70% of the cells were heteroploid, and of these, 50% were tetraploid. No apparent decline in proliferative capacity has been observed after more than twenty-five passages. The properties of this cell line are consistent with those of an immortalized, type-1 astrocyte.

The VMCL-1 cells have a distinctly non-neuronal, glial-like morphology, but lack the large, flattened shape that is typical of type-1 astrocytes in culture Immunocytochemical analysis demonstrated that they stained positive for GFAP and vimentin, and negative for MAP2, A2B5 and O4. The cells were therefore not of the oligodendrocyte lineage. On the basis of a negative reaction to A2B5 and their morphological characteristics they were also not type-2 astrocytes. The classification that is supported by the immunocytochemical evidence is of type-1 astrocytes, although, as noted, these cells lack the classical morphological traits of primary type-1 astrocytes in culture.

EXAMPLE 2

Action of VMCL-1 CM on E14 Dopaminergic Neurons in Culture

VMCL-1 CM was tested at 0, 5, 20 and 50% v/v, for its ability to influence survival and development of E14 mesencephalic dopaminergic neurons in culture. The cultures were primed with 10% fetal bovine serum (FBS) for 12 hours, then grown in a serum-free growth medium thereafter, until they were stained and analyzed after 7 DIV. There was a dose-dependent action of the CM on the increased survival of dopaminergic neurons. The CM increased survival by 5-fold. In contrast, there was no significant increase in non-dopaminergic neuronal survival. The profile of the biological action of this putative factor is quite different from that of CM derived from the B49 glioma cell line, the source of GDNF (Lin et al., Science 260: 1130-1132).

EXAMPLE 3

Gene Expression Analysis of VMCL-1 Cells

To further investigate the similarity between the VMCL-1 cell line and primary cultured astrocytes, we measured the expression of six marker genes characteristic of the mesencephalic region. Analysis of wnt-1, en-1, en-2, pax-2, pax-5, and pax-8 showed that all genes were expressed in both E13 and E14 ventral mesencephalon neural tissue, with the exception of pax-2, which was expressed at E13 but not E14 neural tissue. Both primary astrocytes and VMCL-1 cells expressed wnt-1 at levels comparable with those of E13 and E14 ventral mesencephalic neural tissue. The degree of expression of en-1 was similar in primary astrocytes and VMCL-1 cells, although at a lower level versus expression in E13 and E14 ventral mesencephalic tissue. In contrast, en-2, pax-5 and pax-8 were not expressed in either primary astrocytes or VMCL-1. Pax-2 was expressed in E13 but not E14 ventral mesencephalon, and in primary astrocytes, but not in VMCL-1.

EXAMPLE 4

Chromosomal Analysis of VMCL-1 Cells

Chromosomes were counted in 34 cells. Of these, 9 had a count of 42, the diploid number for rat. Of the 25 cells that were heteroploid, 12/25 or 48% were in the tetraploid range. Hyperdiploid (counts of 43-48) and hypodiploid (counts of 39-41) cells each accounted for 20% of the population, while 12% of the cells had structurally rearranged chromosomes.

The selective action of VMCL-1 CM in increasing the survival of dopaminergic neurons in culture provides a potential clinical use for the molecule(s) produced by this cell line. The lack of a toxic action of VMCL-1 CM at a concentration of 50% v/v indicates that the active, putative neurotrophic factor is not toxic. The action exerted by VMCL-1 CM mirrors almost exactly that of CM prepared from mesencephalic, primary type-1 astrocytes (Takeshima et al., J. Neurosci. 14: 4769-4779, 1994). A high degree of specificity of the putative factor from VMCL-1 for dopaminergic neurons is strongly indicated from the observation that general neuronal survival was not significantly increased, while the survival of dopaminergic neurons was increased 5-fold (FIG. 1). We have demonstrated that primary type-1 astrocytes express GDNF mRNA, but have not detected GDNF protein by Western blot in the CM, at a sensitivity of 50 pg. Moreover, we have shown that under the present experimental conditions, the increased survival of dopaminergic neurons mediated by an optimal concentration of GDNF is never greater than 2-fold. These observations alone indicate that the factor responsible for the neurotrophic actions of VMCL-1 CM is not GDNF.

EXAMPLE 5

Production of Type-1 Astrocyte-Conditioned Medium

E16 type-1 astrocyte CM (10 L) was filtered and applied to a heparin sepharose CL-6B column (bed volume 80 mL) which had previously been equilibrated with 20 mM Tris-HCl (Mallinckrodt Chemical Co. Paris, Ky.) pH 7.6 containing 0.2 M NaCl. After washing with equilibration buffer, bound proteins were eluted from the column with a linear gradient of 0.2 M-2 M NaCl in 20 mM Tris-HCl pH 7.6 (400 mL total volume, flow rate 100 mL/hr). Fractions were collected using a Pharmacia LKB fraction collector and absorbance was measured at 280 nm (Sargent-Welch PU 8600 UV/VIS Spectrophotometer). A 1 mL aliquot was taken from each fraction, pooled into groups of four (4 mL total volume) and desalted using Centricon-10® membrane concentrators (Millipore, Bedford, Mass.). Samples were diluted 1:4 in defined medium and bioassayed for dopaminergic activity. Active fractions were pooled (80 mL total volume) and then applied to a G-75 Sephadex® column (70×2.5 cm, Pharmacia Biotechnology Ltd., Cambridge, UK) which had been pre-equilibrated with 50 mM ammonium formate pH 7.4. Proteins were separated with the same buffer (flow rate, 75 mL/hr) and absorbance was measured at 280 nm A 1 mL aliquot was taken from each fraction, pooled into groups of four (4 mL total volume), concentrated by lyopholyzation and reconstituted in 1 mL distilled water volume. Samples were then diluted 1:4 in defined medium for dopaminergic bioassay. Those with neurotrophic activity were further bioassayed as individual fractions.

An important distinguishing feature of VMCL-1 CM is that it promotes predominantly the survival of dopaminergic neurons, compared with the survival of GABAergic, serotonergic, and other neuronal phenotypes present in the culture. This claim of specificity is also made for GDNF. The results of extensive testing have demonstrated, however, that the VMCL-1-derived compound is not GDNF.

EXAMPLE 6

Isolation and Purification of a Protein Having Dopaminergic Neuronal Survival-Promoting Activity The purification protocol was performed as follows. All salts used were of the highest purity and obtained from Sigma Chemical Co. All buffers were freshly prepared and filtered via 0.2 μM filter (GP Express vacuum-driven system from Millipore)

Step 1: Heparin-Sepharose Column Chromatography (4° C.)

Three liters of VMCL-1 conditioned medium was diluted with an equal volume of 20 mM sodium phosphate buffer, pH 7.2 at room temperature, filtered, and concentrated to 550 mL volume with 5K PREP/SCALE-TFF 2.5 $ft_2$ cartridge (Millipore). The concentrated material was loaded onto a 10 mL Heparin-Sepharose column assembled from 2×5 mL HiTrap Heparin columns (Pharmacia Biotech) and pre-equilibrated with at least 100 mL of 10 mM sodium phosphate buffer, pH 7.2 (buffer A). After the loading was complete, the column was washed with 100 mL of buffer A. A total of 10 fractions were eluted with buffer B (buffer A plus 1 M sodium chloride) in about 3 mL volumes each. A 300 L sample was withdrawn for analysis.

Step 2: Superose 12 Column Chromatography (4° C.)

All of the fractions from step 1 were pooled, then concentrated to 4.5 mL using Centricon Plus-20 concentrator (5,000 MWCO, Millipore), loaded onto 16×600 mm gel-filtration column packed with Superose 12 media (Prep Grade, Sigma Chemical Co.) and pre-equilibrated with at least 300 mL of 20 mM sodium phosphate buffer, pH 7.2 containing 0.6 M sodium chloride (GF buffer). The protein elution was conducted in GF buffer. Two milliliter fractions were collected and analyzed for activity. The active protein was eluted in a 15 mL volume after 84 ml of GF buffer was passed through the column and corresponded to an approximately 20-30 kDa elution region based on the column calibration data obtained with protein standards (Bio-Rad).

Step 3: Ceramic Hydroxyapatite Column Chromatography (Room Temperature; FPLC System)

The active fractions from step 2 that corresponded to the 20-30 kDa elution region were pooled and concentrated to 7.5 mL, using a Centricon Plus-20 concentrator (5,000 MWCO), dialyzed overnight at 4° C. against 2 L of 10 mM sodium phosphate buffer, pH 7.2 (buffer A) and loaded (via Superloop) onto a 1 mL pre-packed ceramic hydroxyapatite (Type I, Bio-Rad) column equilibrated with buffer A. After the excess of unbound protein (flow through) was washed off the column with buffer A, the linear gradient of buffer A containing 1.0 M NaCl was applied from 0 to 100%. One milliliter fractions were collected and analyzed for activity. The active protein was eluted as a broad peak within the region of gradient corresponding to 0.4-0.8 M NaCl concentration.

Step 4: Anion-Exchange Column Chromatography (Room Temperature; FPLC System)

The fractions corresponding to the broad peak were pooled (total volume=15 mL) and concentrated to 6 mL using Centricon Plus-20 (5,000 MWCO), dialyzed overnight at 4° C. against 2 L of 20 mM Tris HCl buffer, pH 7.5 (buffer A), loaded (via Superloop) onto a 1 mL anion-exchange FPLC column (Uno, Bio-Rad), and equilibrated with buffer A. After the excess of unbound protein was washed off the column with buffer A, a linear gradient of 0-100% 1 M NaCl (in buffer A) was applied. One milliliter fractions were collected and analyzed for activity. The active protein was found in the flow-through (i.e., in the unbound protein fraction).

Step 5: BioSil 125 Column Chromatography (Room Temperature; HPLC System)

The active protein fraction from Step 4 (7 mL of total volume) was concentrated down to nearly zero volume (about 1 μL) using Centricon Plus-20 concentrator (5,000 MWCO) and reconstituted in 0.6 mL of 10 mM sodium phosphate buffer, pH 7.2. The reconstituted material (70 μL, analytical run) was loaded onto BioSil 125 HPLC gel-filtration column (Bio-Rad) equilibrated with 20 mM sodium phosphate buffer, pH 7.2 (GF buffer). The chromatography was conducted using HP 1100 Series HPLC system (Hewlett-Packard). The eluate was collected in 120 μL fractions and analyzed for activity and protein content (SDS-PAGE). The activity was found in fractions associated with the main 280-nm absorbance peak eluted from the column, which was represented by a 45-kDa protein according to SDS-PAGE analysis. Nevertheless, no activity was found in the side fractions of the 45-kDa protein peak, indicating that activity might be due to the presence of another protein that was co-eluted with 45 kDa protein, but at much lower concentration that could not be detected on the 12% SDS-PAGE silver-stained gel. Therefore, the remaining concentrated material from step 5 was further concentrated down to 80 μL volume using a Centricon-3 concentrator (Millipore), and 60 μL was loaded and separated on the column at the same conditions as for the above-described analytical run. Aliquots of 8 μL were taken from each 120 μL fraction of the eluate and analyzed by SDS-PAGE (12% gel) combined with silver staining. This analysis indicated that another two additional proteins (having molecular weights of about 18 and 20 kDa) were associated with the active fractions and co-eluted with the major 45-kDa protein. The active fractions were dialyzed against 1 L of ammonium acetate buffer, pH 8.0 (4° C.) and combined to create two active pools, P-1 and P-2, such that P-1 contained the 20 kDa protein and the 45 kDa protein, and P-2 contained the 18 kDa protein and the 45 kDa protein. Each pool was dried down on SpeedVac vacuum concentrator (Savant) and separately reconstituted in 15 μL 0.1 M ammonium acetate buffer, pH 6.9. Aliquots were withdrawn from each sample and assayed for activity. Additionally, 1 μL aliquots were subjected to 12% SDS-PAGE analysis followed by silver staining.

The results of the foregoing analysis clearly indicated that P-1, but not P-2, contained the desired survival-promoting activity. In the next step, both P-1 and P-2 were dried on SpeedVac, reconstituted (each) in 10 μL of freshly prepared SDS-PAGE reducing sample buffer (Bio-Rad), incubated for one minute in a boiling water bath and loaded onto a 12% SDS-PAGE gel. After electrophoresis was complete, the gel was fixed in methanol/acetic acid/water solution (50:10:40) for 40 minutes at room temperature, washed three times with nanopure water, and stained overnight with GelCode Blue Stain Reagent (Pierce) at room temperature. After staining was completed, and the GelCode solution was washed off the gel with nanopure water, the visible protein bands corresponding to the 45 kDa protein (both P-1 and P-2) and the 20 kDa protein (P-1 only) were excised from the gel with a razor blade. Each gel slice containing a corresponding band was placed in a 1.5 mL microcentrifuge tube until the time of in-gel digestion.

EXAMPLE 7

Analysis of In-Gel Digested Fragments by nESI-MS/MS

The protein gel bands were incubated with 100 mM ammonium bicarbonate in 30% acetonitrile (aq.) at room temperature for 1 hour in order to remove the colloidal comassie blue stain. The destaining solution was replaced a number of times until the dye was completely removed. The gel pieces were then covered with deionized water (~200 μL) and shaken for 10 minutes. The gel pieces were dehydrated in acetonitrile and, after removing the excess liquid, were dried completely on a centrifugal evaporator. The gel bands were rehydrated with 20 μL of 50 mM ammonium bicarbonate, pH 8.3, containing 200 ng of modified trypsin (Promega, Madison, Wis.). The gel pieces were covered with 50 mM ammonium bicarbonate, pH 8.3 (approximately 50 μL), and were incubated overnight at 37° C. The digest solutions were then transferred to clean eppendorf tubes and the gel pieces were sonicated for 30 minutes in 50-100 μL of 5% acetic acid (aq). The extract solutions were combined with the digest solutions and evaporated to dryness on a centrifugal evaporator.

The in-gel digest extracts were first analyzed by matrix-assisted laser desorption ionization-time of flight mass spectrometry (MALDI-TOFMS) using a Voyager Elite STR MALDI-TOFMS instrument (Applied Biosystems Inc., Framingham, Mass.). The extracts were dissolved in 5 μL of 50% acetonitrile, 1% acetic acid. Dihydroxybenzoic acid was used as the matrix and spectra were acquired in positive ion, reflectron mode. Approximately one fifth of each sample was used for this analysis. These spectra provided the masses of the peptides in the digest extracts which were then used to search an in-house, non-redundant protein sequence database, a process called peptide mass fingerprinting. The remainder of the samples were used for peptide sequencing analysis by nanoelectrospray ionization-tandem mass spectrometry (nESI-MS/MS). The extracts were first desalted using C18 ZipTips (Millipore) and redissolved in 75% methanol (aq.), 0.1% acetic acid (5 μL). Approximately one half of the samples were loaded into nanoelectrospray glass capillaries (Micromass). nESI-MS/MS analyses were carried out using a Q-Star quadrupole time-of-flight hybrid mass spectrometer (PE SCIEX, Concord, ON). All MS/MS analyses were carried out in positive ion mode. The collision gas was nitrogen and the collision energy was 40-60 eV. MS/MS spectra were typically acquired every second over a period of two minutes. The MS/MS spectra were used to search an in-house non-redundant protein sequence database using partial sequence tags (i.e., only the peptide mass and a few fragment ions are used to search the database). If the protein was not identified by this procedure then the amino acid sequences of two or more peptides were determined as fully as possible from the MS/MS spectra. These sequences were used to carry out BLAST searches on NCBI's protein, nucleotide and EST sequence databases.

EXAMPLE 8

Identification of MANF, a Secreted Form of ARP

In order for ARP to be a factor that is responsible at least in part for the observed neurotrophic activity of VMCL-1 CM, the protein must be released from the cell. The predicted amino terminus of ARP has basic charges, however, a property that would favor retention in the cell nucleus. Nonetheless, we hypothesized that there would also exist a secreted form.

Support for our hypothesis was found in a publication by Goo et al. (Molecules and Cells 9:564-568, 1999), who identified a cDNA encoding an ARP-like protein in *Drosophila melanogaster* while screening a cDNA library using a yeast signal sequence trap technique. The putative ARP-like protein encoded by this cDNA lacks the arginine-rich amino terminus. Using the SignalP program, we identified a signal peptide (residues 1-22) and a signal peptidase-cutting site between alanine 22 and leucine 23 of *Drosophila* ARP-like protein, providing additional evidence that *Drosophila* ARP-like protein is secreted.

Based on the alignment between human ARP and *Drosophila* ARP-like protein, we postulated that human ARP would have a signal sequence and signal peptidase cutting site. Accordingly, we used the SignalP program to analyze the human ARP lacking the arginine-rich amino terminus (amino acids 1-55); this polypeptide is now referred to as pro-MANF. In this example, the methionine at position 56 is the start codon. The SignalP program predicted a signal peptide consisting of residues 1-21 of SEQ ID NO: 2 and a cutting site between alanine 21 and leucine 22, which is consistent with the results from the analysis of the *Drosophila* ARP-like protein. The predicted cleaved human MANF protein is depicted in FIG. 2 and SEQ ID NO: 3. This and other exemplary MANF polypeptides are shown in FIGS. 2 and 3. Exemplary MANF polynucleotides are shown in FIG. 4.

Based in part on our analysis of *Drosophila* ARP-like protein (GenBank Accession No. AF132912_1) and human ARP, we predict that the translation can begin at either the methionine at position 1 or the methionine at position 56 of human ARP. In the latter case, the signal peptide-containing protein (pro-MANF) is capable of being secreted from the cell in the form of MANF, where the protein acts a neurotrophic factor. Our discovery of the existence of MANF does not, however, preclude an intracellular function for the ARP containing the arginine-rich amino-terminal region.

EXAMPLE 9

Biological Activity of MANF Expressed in *E. Coli*

Figure 5:
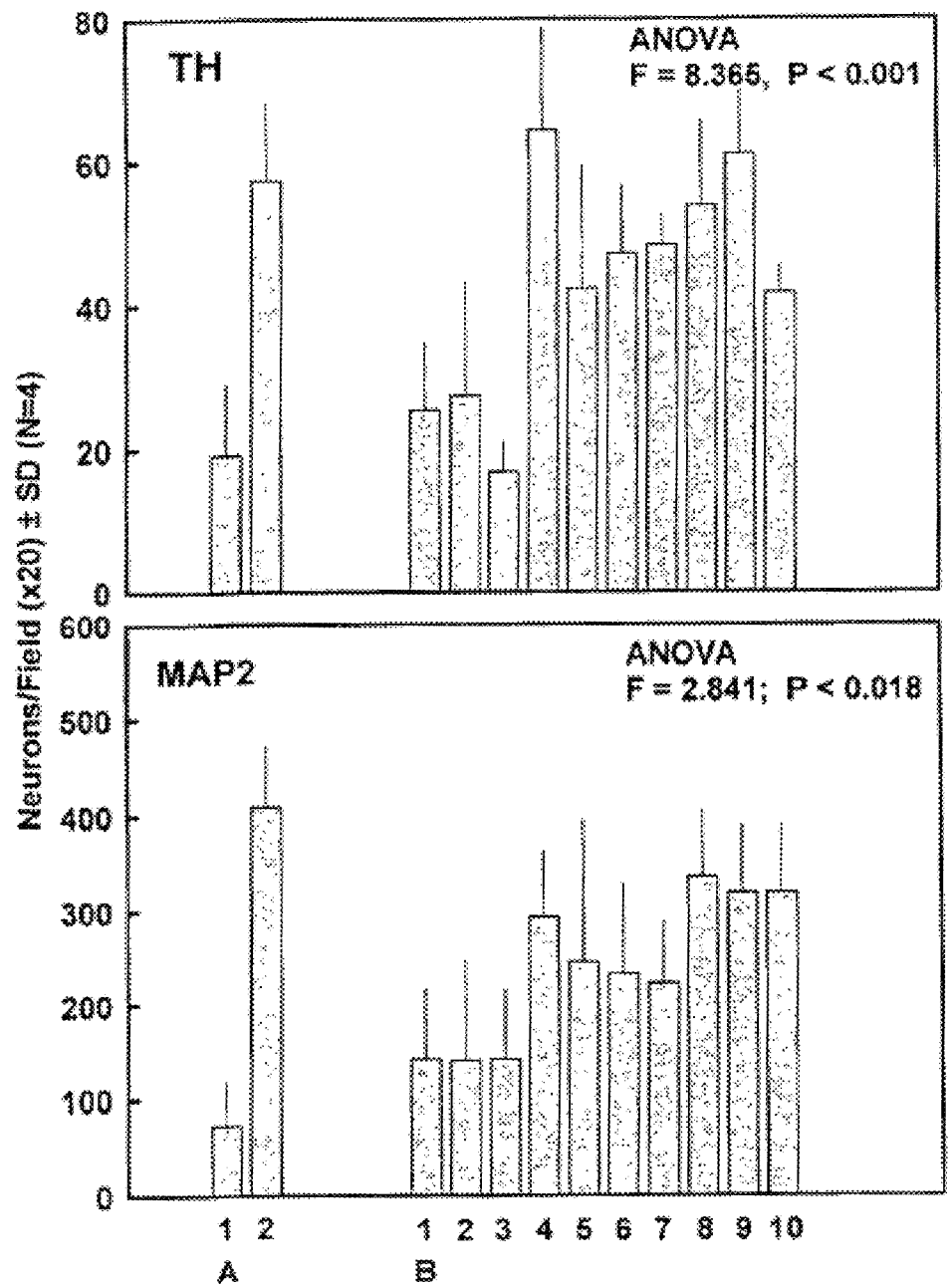
FIG. 5 is a schematic illustration showing the biological activity of MANF expressed in *E. Coli* on the survival of tyrosine hydroxylase-positive cells (top panel) and MAP2-positive cells (bottom panel). The lanes are as follows: A1-PCM0 control; A2-VMCL-1 CM (25%); B1-MANF (10 pg/mL); B2-MANF (50 pg/mL); B3-MANF (100 pg/mL); B4-MANF (250 pg/mL); B5-MANF (500 pg/mL); B6-MANF (1 ng/mL); B7-MANF (5 ng/mL); B8-MANF (10 ng/mL); B9-MANF (50 pg/mL); B10-MANF (100 ng/mL).

Recombinant protein expression was carried out in *E. Coli* bacterial cells using pTriEx containing a polynucleotide encoding human MANF (SEQ ID NO: 3). A total of 4 mg of purified recombinant MANF was obtained from 350 mL of bacterial cell culture, its identity confirmed by mass spec sequencing. This protein was tested for its ability to protect DA neurons. As shown in FIG. 5, MANF expressed in *E. Coli* was capable of protecting DA neurons from cell death to the same extent as did the VMCL-1 conditioned medium.

EXAMPLE 10

Dose-Response for Eukaryotic MANF Expressed in HEK293 Cells

The dose-relationship of human MANF (99% pure, produced in HEK293 cells) versus survival of dopaminergic neurons was tested using a dopaminergic cell culture assay system containing 20% of dopaminergic neurons. E14 pregnant rats were killed by $CO_2$ narcosis. The torso was soaked in 70% EtOH, a laporatomy was performed, and the uterine sac removed and transferred to a 50 mL tube containing 20 mL cold HBSS, pH 7.4. Each uterine sac was in turn transferred to a 10-cm petri dish containing 15 mL cold HBSS. The fetuses were removed intact, and each brain was isolated intact and transferred to a new 10-cm petri dish containing 15 mL cold HBSS. The medial ventral mesencephalon (VM) at the roof of the mesencephalic flexure was dissected to obtain 1.0 $mm^3$ piece of tissue at a packing density of $1.0 \times 10^5$ cells/$mm^3$. The VM tissue was transferred to a 15 mL tube containing 10 mL of cold PCM10. The pooled VM tissue was washed with PCM10 (DMEM/F12 with 2 mM glutamine, 5 mg/mL insulin, 5 mg/mL transferrin, 5 mg/mL sodium selenite; 20 nM progesterone, 30 nM thyroxine, and 10% fetal bovine serum) (three washes), followed by a single wash in serum-free medium (PCM0; same as PCM10 except that it lacks fetal bovine serum) and digested in 2.0 ml of PCM0 containing papain (10 U/mL) for 15 minutes, at 37° C. The tissue was then rinsed (3×5 mL) with PCM10, to inactivate the protease activity. Trituration was done in 2.0 mL of PCM0, using a P-1000 set at 500 µL. The end point is a milky suspension with no signs of tissue clumps. The dispersed cells were centrifuged (1,000 rpm, 2 min, 4° C.), counted, then resuspended at a density of $6.25 \times 10^5$ cells/mL in PCM10. Cell viability was tested at this stage, and was usually >95%.

The cells were plated as microisland (MI) droplets of 25 µL, ($1.56 \times 10^4$ cells/MI) on 8-well chamber slides, coated with poly-D-lysine. A 25 µL MI droplet occupies an area of 12.5 $mm^2$. The average, final, mean cell density of the MI is therefore $1.25 \times 10^5$ cells/$cm^2$. The mean cell density at the center of the MI is about $2.0 \times 10^5 / cm^2$, falling off to $<1.0 \times 10^4$ at the periphery of the MI. The MIs were incubated at 37° C., in 5% $CO_2$ at 100% humidity for 45 minutes to allow the cells to attach to the coated surface. After attachment, 375 µL of PCM10 was added to each well, and the cells serum-primed for 4 hr. At the end of priming, 100% of PCM10 was aspirated, and replaced with serum-free, PCM0.

MANF was prepared as follows. Human pro-MANF (SEQ ID NO: 2) was cloned into a pTriEx expression vector. Recombinant protein expression was carried out in HEK293 cells. Twenty micrograms of purified recombinant MANF lacking the signal sequence) was obtained from 800 mL of HEK293 cell conditioned medium. Its identity was confirmed by mass spec sequencing analysis.

Cultures were treated on the first, third and fifth days with the indicated amount of MANF. The cultures were fixed and stained on DIV6 or DIV7, using either the Vector ABC method, or indirect immunofluorescence.

Figure 6:
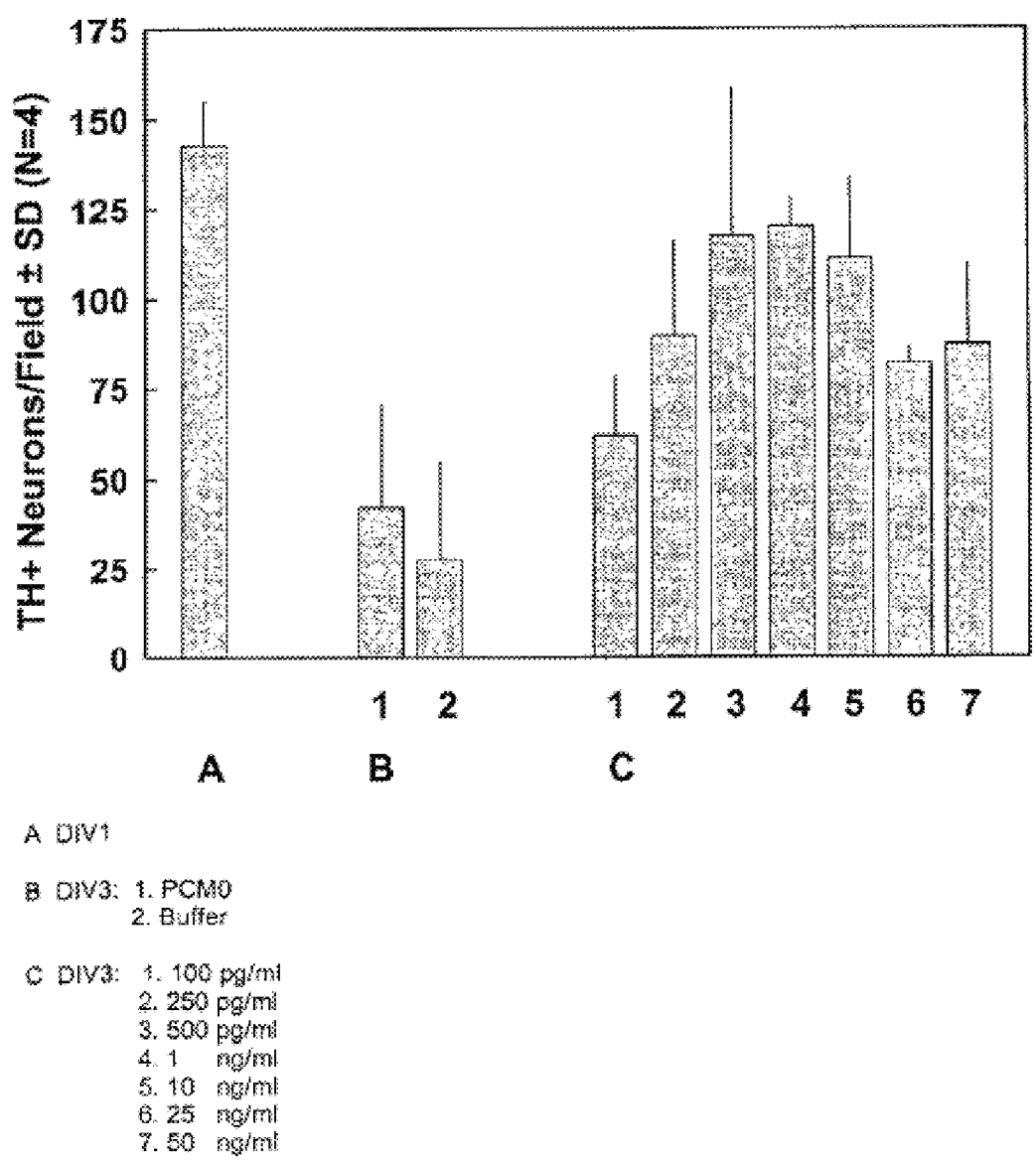
FIG. 6 is a schematic illustration showing the dose-response curve for MANF expressed and secreted from HEK293 cells. The lanes are as follows: A-control; B1-PCM0 control; B2-buffer control; C1-MANF (100 pg/mL); C2-MANF (250 pg/mL); C3-MANF (500 pg/mL); C4-MANF (1 ng/mL); C5-MANF (10 ng/mL); C6-MANF (25 ng/mL); C7-MANF (50 pg/mL). All data were collected were DIV3, except for A, which was at DIV1.

As early as DIV3, there was a significant difference between the different concentrations of MANF tested (ANOVA, P<0.001) (FIG. 6). Paired comparisons using the Tukey method of analysis, indicated that MANF at 250 and 500 pg/ml and 1.0 and 10 ng/nL were significantly different from controls (P<0.05).

EXAMPLE 11

Rank Order of Potency among BDNF, GDNF and MANF

Figure 7:
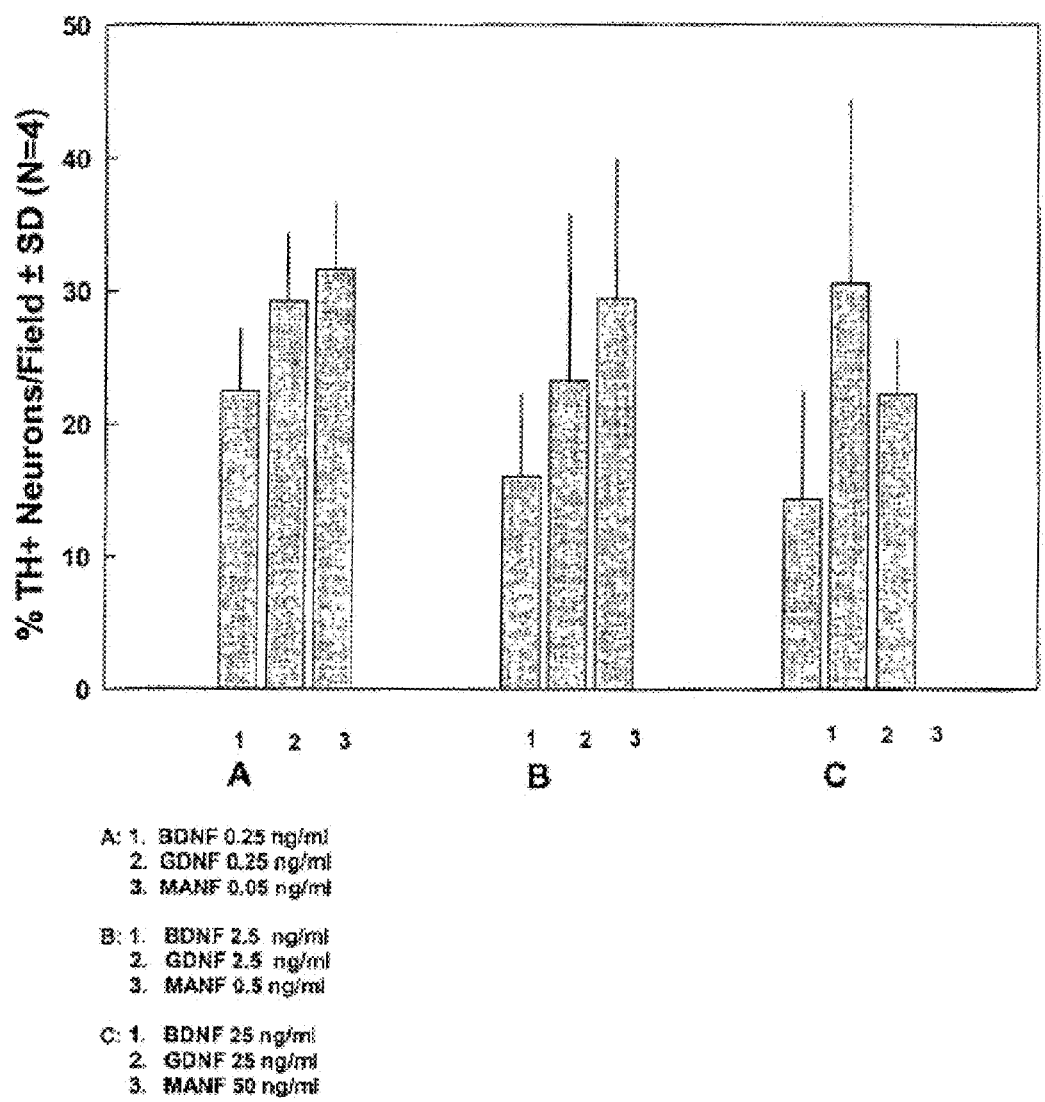
FIG. 7 is a schematic illustration showing the rank order potency of BDNF, GDNF, and MANF.

As illustrated in FIG. 7, when three equivalent doses of BDNF, GDNF and MANF were tested, the rank order of potency was: MANF>GDNF>BDNF, indicating that the two lower concentrations of MANF were more selective for DA neurons, relative to low doses of BDNF or GDNF. At the highest dose, the rank order of potency was: GDNF>MANF>BDNF. In general, BDNF tended to be the most potent, but least specific for protecting DA neurons. At lower concentrations, MANF tended to be the most selective in protecting DA neurons.

EXAMPLE 12

Domains of MANF Predicted to be Active

We have identified three peptides from MANF that we predict may have MANF biological activity (i.e., protect DA neurons from cell death). The human peptides are LRPGDCEVCISYLGRFYQDLKDRDVTFSPATIENELIKFCREA; SEQ ID NO: 11; RGKENRLCYYIGATDDAATKIINEVSKPLAHHIPVEKIC E KLKKKDSQICEL; SEQ ID NO: 12 and KYDKQIDLSTVDLKKLRVKELKKI LDDWGETCKGCAEKSDYIRKINELMPKY; SEQ ID NO: 13. Counterpart peptides can be readily identified using standard sequence alignment programs. MANF sequences for mouse, cow, and pig are provided herein. These peptides can be employed in any of the therapeutic methods described herein, and are expressly considered to be "MANF polypeptides."

EXAMPLE 13

Selectivity of Responsiveness to MANF

The ability of MANF to protect neurons from other brain regions was tested. No protection of rat cerebellar granule neurons, nodose sensory neurons, or sympathetic noradrenergic neurons was observed. Similarly, in ventral mesencephalic cultures, there appeared to be no activity on GABAergic and serotonergic neurons in cultures in which MANF was demonstrably protective for DA neurons. In contrast to the foregoing results, MANF was protective for a subset of dorsal root ganglion cells in culture. Dorsal root ganglia consist of at least three sub-populations of neurons. It has been demonstrated that NGF, BDNF and NT-3, all members of the neurotrophin family of neurotrophic factors, each acts on a different subset of these neurons. The action of MANF on this subset of dorsal root ganglion neurons, is therefore in keeping with the general neuroprotective properties of neurotrophic factors.

EXAMPLE 14

Production of MANF Polyclonal Antibodies

Polyclonal antibodies were prepared as follows. His-tagged full length MANF was prepared in *E. Coli*. Six antigen injections of 200 µg of purified MANF protein per injection per rabbit were performed (one each on days 1, 21, 35, 49, 63, and 70). The serum was collected on day 84 (100 mL serum/rabbit).

Figure 8:
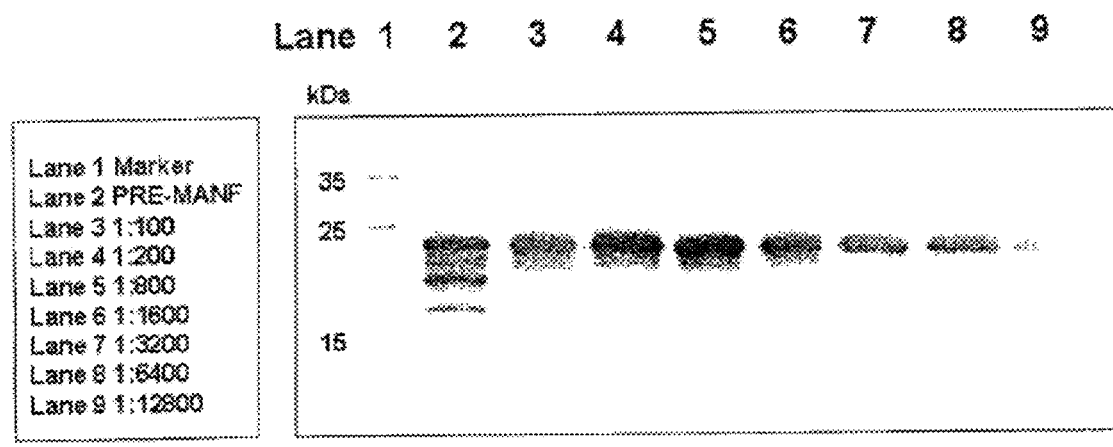
FIG. 8 is a schematic illustration showing MANF polyclonal antibody activity in western blots of MANF (720 ng).
Figure 9:
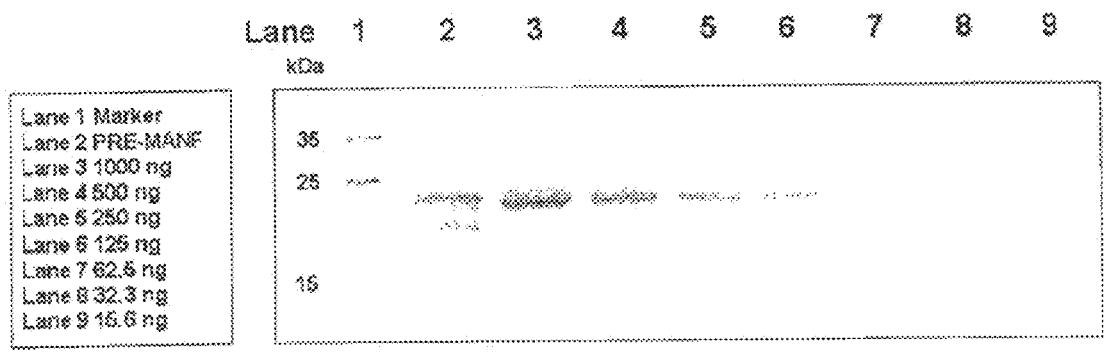
FIG. 9 is a schematic illustration showing the sensitivity of MANF polyclonal antibody detection in western blots of MANF. As little as 15.6 ng MANF was detectable.
Figure 10:
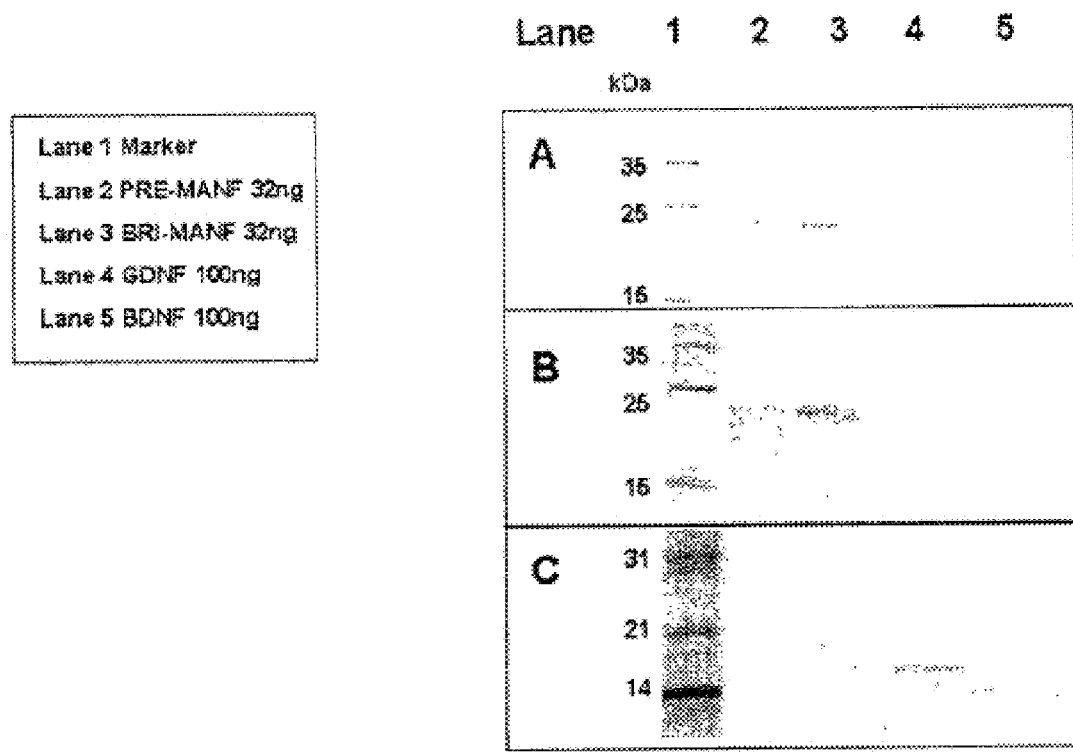
FIGS. 10A-10C are a series of schematic illustrations showing that MANF polyclonal antibody did not cross-react with BDNF or GDNF. (A) western blot; (B) silver stain; (C) coomassie blue stain.

Western blot analysis was used to test the activity of MANF-pAb. A relatively high quantity of MANF (720 ng) was used for the initial test of the activity of MANF-pAb, which remained active at a dilution of 1:12,800 (FIG. 8; lane 9). In the next test, the dilution of MANF was fixed at 5,000 and the quantity of MANF varied from 1,000 to 15.6 ng. The lowest quantity of MANF, 15.6 ng, was easily detected (FIG. 9, lane 9). In tests for cross reactivity with BDNF and GDNF, the results showed that even at three times the quantity of MANF (32 ng), the MANF-pAb did not cross react with either BDNF or GDNF (FIGS. 10A-10C).

The foregoing results were obtained with the following methods.

Mesencephalic Cultures

Primary mesencephalic cell culture was prepared from timed-pregnant Sprague-Dawley rats (Taconic Farms; Germantown, N.Y.). as described previously (Shimoda et al., Brain Res. 586:319-323, 1992; Takeshima et al., J. Neurosci. 14:4769-4779, 1994; Takeshima et al., Neuroscience. 60:809-823, 1994; Takeshima et al., J. Neurosci. Meth. 67:27-41, 1996). The dissected tissue was collected and pooled in oxygenated, cold (4° C.), HBSS or medium containing 10% fetal bovine serum (Biofluids Laboratories, Rockville, Md.), depending on the purpose of the experiment. Pregnant rats were killed by exposure to $CO_2$ on the fourteenth gestational day (i.e., E14), the abdominal region was cleaned with 70% EtOH, a laparotomy was performed, and the fetuses collected and pooled in cold Dulbecco's phosphate-buffered saline (DPBS), pH 7.4, without $Ca^{2+}$ or $Mg^{2+}$. The intact brain was then removed, a cut was made between the diencephalon and mesencephalon, and the tectum slit medially and spread out laterally. The ventral, medial 1.0 $mm^3$ block of tissue comprising the mesencephalic dopaminergic region was isolated. Dissected tissue blocks were pooled in cold (4° C.), oxygenated medium. The tissue was triturated without prior digestion. Alternatively, the cells were incubated in L-15 growth medium containing papain (Sigma Chemical Co.), 10 U/mL, at 37° C., for 15 minutes, washed (3×2 mL) with medium, and triturated using only the needle and syringe. The dispersed cells were transferred to 1.5 mL Eppendorf tubes (1.0 mL/tube), and centrifuged at ~600 g for 2 minutes. The use of higher centrifugation speeds for longer periods results in contamination of the cultures with debris and, as a result, suboptimal growth of the cells. The medium was carefully aspirated, and the cells resuspended in fresh medium and counted using a hemocytometer. All procedures, from laparotomy to plating were completed within 2 hours. In a typical experiment, one litter of 10-15 fetuses yielded $1.0 \times 10^5$ cells/fetus, or $1.0 \times 10^6$-$1.5 \times 10^6$ cells/litter.

Mesencephalic Microisland Cultures

To make mesencephalic microisland cultures, cells were prepared as described above, and resuspended at a final density of $5.0 \times 10^5$ mL. A 25 uL droplet of the suspension ($1.25 \times 10^4$ cells) was plated using a 100 µL pipette onto 8-well chamber slides coated with poly-D-lysine (50 µg/mL). The area of the droplet was ~12.5 $mm^2$, for a final mean cell density of $1.0 \times 10^5/cm^2$. The droplet was dispensed uniformly, and the pipette tip withdrawn vertically, to avoid smearing. The area occupied by the microisland culture remained uniform for the duration of the culture. The cultures were incubated for 30 minutes at 37° C., in 5% $CO_2$ at 100% humidity, to allow the cells to attach, and 375 µL of growth medium was then added to each well. The medium was changed after the first 12 hours, and approximately half of the medium was changed every second day thereafter.

Cell Viability Assay

A two-color fluorescence cell viability assay kit (Live/Dead Viability/Cytotoxicity Assay Kits, #L-3224, Molecular Probes, Inc., Eugene, Oreg.) was used to identify live and dead cells prior to plating and in cultures. Live and dead cells fluoresced green and red, respectively, giving two positive indicators of viability. Ethidium homodimer and calcein-AM were diluted with DPBS to give final concentrations of 3.8 µM and 2.0 µM, respectively. Evaluation of cell viability was done before plating. A cell suspension was incubated for 15 minutes with an equal volume of dye (typically 20 µL) on glass slides at room temperature in a dark, humid chamber, coverslipped, and then examined with a fluorescent microscope using FITC optics. Cell viability just before plating was about 95%.

Culture

The serum-free medium used consisted of equal volumes of Dulbecco's modified Eagle medium (DMEM) and Ham's F-12 (Gibco, Grand Island, N.Y.; 320-1320AJ), 1.0 mg/mL bovine albumin fraction V (Sigma Chemical Co.; A4161), 0.1 µg/mL apo-transferrin (Sigma; T-7786), 5 µg/mL insulin (Sigma; I-1882), 30 nM L-thyroxine (Sigma; T-0397), 20 nM progesterone (Sigma; P-6149), 30 nM sodium selenite (Sigma; S-5261), 4.5 mM glutamine (Gibco, 320-5039AF), 100 U/mL penicillin, and 100 µg/mL streptomycin (Gibco; P-100-1-91).

Preparation of Conditioned Medium from VMCL-1 Cell Line

In preparing conditioned medium from the VMCL-1 cell line, $2.0 \times 10^6$ cells were plated in a 15 cm uncoated culture dish, in 20 mL of growth medium containing 1.0% of FBS. At 80% confluence, the medium was aspirated and the cells washed once with serum-free medium. 20 mL of serum-free N2 medium without albumin was added, and conditioning allowed to continue for 48 hours. During this time, the cells usually expanded to 100% confluence. The medium was aspirated, pooled in 50 mL tubes, centrifuged (15,000 rpm for 20 minutes) and subsequently pooled in a 1.0 L plastic bottle.

Usually 5 mL of each batch of CM was filter-sterilized using a 0.22 μm filter, stored at aliquots of 5 mL, at −70° C., and used to determine neurotrophic potency, before being pooled with the larger store of CM. If desired, VMCL-1 CM can be made in large quantities using standard industrial cell culture techniques known to those in the art.

Production of Conditioned Medium for Type-1 Astrocytes

Type-1 astrocytes were prepared as follows. E16 rat fetal brain stem was dissected in cold DPBS, and the mesencephalic region transferred to astrocyte culture medium (DMEM/Ham's F-12, 1:1, 15% FBS, 4.0 mM glutamine, 30 nM sodium selenite, penicillin, and streptomycin). Cells were dispersed by trituration in 2 mL of fresh medium using an 18-gauge needle fitted to a syringe. Cells were centrifuged for 5 minutes at 2,000 rpm in a centrifuge, re-suspended in medium, and triturated again. The final cell pellet was dispersed and plated at a density of $1 \times 10^6$ cells/75 cm² flask in 15 mL of medium. Cells were incubated at 37° C. in an atmosphere of 5% carbon dioxide and 95% air for 24 hours, and unattached cells were removed by aspiration. Cells were cultured for an additional nine days, and flasks were then shaken vigorously for 16 hours to remove any contaminating cell types. Astrocyte monolayers were washed three times with DPBS, trypsinized and replated (density of $1 \times 10^6$ cells/flask). At this time, a small proportion of the cells were plated onto eight-well chamber slides (Nunc Inc., Naperville, Ill.); these sister cultures were treated as described for the flask cultures. At confluence, the medium was replaced with medium containing 7.5% FBS and cells were incubated for 48 hours. At the next exchange, defined serum-free medium (DMEM/Ham's F-12, 1:1, 4.0 mM glutamine, 30 nM sodium selenite, penicillin 100 U/ml and streptomycin 100 U/mL) was added and cells were incubated for a further 48 hours. Medium was replaced and, after five days, conditioned medium was harvested and mixed with leupeptin (10 mM: Bachem, Torrance, Calif.) and 4-(2-aminoethyl)-benzenesulfonyl fluoride hydrochloride (1.0 mM: ICN Biochemicals, Aurora, Ohio) to inhibit proteolysis. At the time of harvesting, astrocyte monolayers cultured on chamber slides were immunostained in order to assess the culture phenotype.

Culturing of VMCL-1 Cells

In culturing VMCL-1 and preparing VMCL-1 CM, $2.0 \times 10^6$ cells were plated in a 15-cm uncoated culture dish, in 20 mL growth medium initially containing 10% FBS. At 80% confluence, the medium was aspirated and the cells washed once with serum-free medium. Usually 20 mL of serum-free medium without albumin was added, and conditioning allowed to continue for 48 hours. N2 medium proved to be particularly suitable for use to collect conditioned medium. During these 48 hours, the cells usually expanded to 100% confluence. The medium was aspirated, pooled in 50 mL tubes, centrifuged (15,000 rpm, 20 min) and pooled in a 1.0 L plastic bottle. Approximately 5 mL of each batch of CM was sterilized using a 0.22 mm filter, stored at aliquots of 0.5 mL, at −70° C., and used to determine neurotrophic potency, before being pooled with the larger store of CM. The VMCL-1 cell line has now been passaged greater than 50 times.

Immunocytochemistry

For MAP2 and TH immunocytochemistry, the cultures were washed (2×250 μL) with cold DPBS, fixed with 4% formaldehyde in PBS for 10 minutes, permeabilized using 1% $CH_3COOH$/95% EtOH at −20° C., for 5 minutes, and then washed (3×250 μL) with PBS. Non-specific binding was blocked with 1% bovine serum albumin in PBS (BSA-PBS) for 15 minutes. Anti-TH antibody (50 μL) (Boehringer-Mannheim, Indianapolis, Ind.), or anti-MAP2 antibody (Boehringer-Mannheim) was applied to each well, and the slides incubated in a dark humid box at room temperature for 2 hours. Control staining was done using mouse serum at the same dilution as the anti-TH antibody. After washing (2×250 μL) with PBS, anti-mouse IgG-FITC (50 μL) was applied, and the slides incubated for an additional 1 hour. After washing with PBS (2×250 μL), excess fluid was aspirated, the chamber walls removed, and a single drop of VectaShield mounting medium (Vector Laboratories, Burlingame, Calif.) applied, followed by a cover glass, which was sealed with nail polish. In some experiments, TH was identified using biotinylated, secondary antibodies, and the nickel-enhanced, diaminobenzidine (DAB) reaction product was developed using the biotinylated peroxidase-avidin complex (ABC kit; Vector Laboratories).

For glial fibrillary acidic protein (GFAP, Boehringer-Mannheim, #814369), fixation and permeabilization were done in one step using 5% $CH_3COOH$/95% $C_2H_5OH$ at −20° C. The subsequent procedures were the same as those used to visualize TH. For A2B5 and O4, the cultures were washed with cold DPBS (2×250 μL) and blocked with 1% BSA-PBS for 10 minutes. The A2B5 antibody (50 μL) was applied to each well, and incubated for 1 hour. After washing with DPBS (2×250 μL), the secondary antibody, anti-IgM-FITC, was applied for 30 minutes. The cells were then washed with DPBS (2×250 μL). To counter-stain cell nuclei, cells were incubated with 0.5 μg/mL of nucleic acid dye H33258 (Hoechst, Kansas City, Mo.) in 10 mM sodium bicarbonate for 15 minutes at room temperature, then rinsed in PBS for 2×10 minutes. After a final washing with cold DPBS (2×250 μL), they were mounted as described above.

RT-PCR Analysis

Total RNA was extracted from rat E13 or E14 ventral mesencephalic tissue or from $1 \times 10^9$ astrocytes or from $1 \times 10^9$ VMCL-1 cells using RNA-STAT reagent (TelTest, University of Maryland, Baltimore, Md.). First strand cDNA was generated from RNA and amplified by polymerase chain reaction using the manufacturer's procedures.

Reaction products were resolved by 2% agarose gel electrophoresis to determine size and relative abundance of fragments. PCR results for b-actin and GAPDH were included as controls to confirm equal loading of cDNA.

Chromosomal Analysis

The cells were grown in DMEM/F-12 1:1 medium supplemented with 2.5% FBS, D-glucose (2.5 g/L) and ITS supplement, diluted 1:100. Twenty-four hours later, subcultures at metaphase stage were arrested with colchicine (10 μg/mL). The cells were trypsinized and subjected to hypotonic shock (75 mM KCl). The cells were then fixed in three changes of MeOH/$CH_3COOH$, 3:1, and air-dried. The cells were then stained using 4% Geisma, and microscopically examined.

Deposit

Applicant has made a deposit of at least 25 vials containing cell line VMCL-1 with the American Type Culture Collection, Manassas Va., 20110 U.S.A., ATCC Deposit No. PTA-2479. The cells were deposited with the ATCC on Sep. 18, 2000. This deposit of VMCL-1 will be maintained in the ATCC depository, which is a public depository, for a period of 30 years, or 5 years after the most recent request, or for the effective life of the patent, whichever is longer, and will be replaced if it becomes nonviable during that period. Additionally, Applicant has satisfied all the requirements of 37 C.F.R. §§1.801-1.809, including providing an indication of the viability of the sample. Applicant imposes no restrictions on the availability of the deposited material from the ATCC. Applicant has no authority, however, to waive any restrictions imposed by law on the transfer of biological material or its transportation in commerce. Applicant does not waive any infringement of its rights granted under this patent.

Other Embodiments

All publications and patents mentioned in the above specification are herein incorporated by reference. Various modifications and variations of the described method and system of the invention will be apparent to those skilled in the art without departing from the scope and spirit of the invention. Although the invention has been described in connection with specific preferred embodiments, it should be understood that the invention should not be unduly limited to such specific embodiments. Indeed, various modifications of the described modes for carrying out the invention which are obvious to those skilled in molecular biology or related fields are intended to be within the scope of the invention.

What is claimed is:

1. A MANF polypeptide, wherein the amino acid sequence of the MANF polypeptide consists of a sequence at least 95% identical to SEQ ID NO: 4 and an N-terminal methionine residue.

2. The MANF polypeptide of claim 1, wherein the amino acid sequence of the MANF polypeptide consists of a sequence at least 97% identical to SEQ ID NO: 4 and the N-terminal methionine residue.

3. The MANF polypeptide of claim 1, wherein the N-terminal methionine residue is the N-terminal methionine residue of SEQ ID NO: 4.

4. A composition comprising at least 60% by weight of a mesencephalic astrocyte-derived neurotrophic factor (MANF) polypeptide, wherein the amino acid sequence of the MANF polypeptide consists of a sequence at least 95% identical to SEQ ID NO: 4 and an N-terminal methionine residue.

5. The composition of claim 4, wherein the amino acid sequence of the MANF polypeptide consists of a sequence at least 97% identical to SEQ ID NO: 4 and the N-terminal methionine residue.

6. The composition of claim 4, wherein the amino acid sequence of the MANF polypeptide consists of the sequence of SEQ ID NO: 4.

7. A pharmaceutical composition comprising the composition of claim 4.

8. The pharmaceutical composition of claim 7, wherein the pharmaceutical composition is in the form of a liquid.

9. The pharmaceutical composition of claim 7, wherein the pharmaceutical composition is a solution or suspension.

10. The pharmaceutical composition of claim 7, wherein the pharmaceutical composition further comprises an additional active ingredient.

11. The pharmaceutical composition of claim 7, wherein the pharmaceutical composition further comprises a neural cell.

12. The pharmaceutical composition of claim 11, wherein the neural cell is selected from the group consisting of a neuron, a neural stem cell, and a neuronal precursor cell.

13. The pharmaceutical composition of claim 7, wherein the N-terminal methionine residue is the N-terminal methionine residue of SEQ ID NO: 4.

14. A method for treating Parkinson's disease in a subject by administering to the subject an effective amount of the pharmaceutical composition of claim 7.

15. The method of claim 14, wherein the subject is a human.

16. The method of claim 14, further comprising transplanting a cell into the subject.

17. The method of claim 16, wherein the pharmaceutical composition is administered to said subject in a time window from four hours before said transplanting to four hours after said transplanting.

18. The method of claim 16, wherein the pharmaceutical composition is administered to said subject in a time window from two hours before said transplanting to two hours after said transplanting.

19. The method of claim 14, wherein the method reduces dopaminergic neuronal cell death in said subject.

20. The method of claim 14, wherein the method increases dopaminergic neuronal cell survival in said subject.

21. The method of claim 14, wherein the N-terminal methionine residue is the N-terminal methionine residue of SEQ ID NO: 4.

22. An in vitro method of increasing the survival of dopaminergic neurons, comprising contacting the dopaminergic neurons with a survival-promoting amount of a MANF polypeptide, wherein the amino acid sequence of the MANF polypeptide consists of a sequence at least 95% identical to SEQ ID NO: 4 and an N-terminal methionine residue.

23. The method of claim 22, further comprising expanding the dopaminergic neurons, thereby generating expanded dopaminergic neurons.

24. The method of claim 23, wherein the expanded dopaminergic neurons are capable of being transplanted.

25. The method of claim 22, wherein the N-terminal methionine residue is the N-terminal methionine residue of SEQ ID NO: 4.

26. A method for determining whether a candidate compound modulates MANF-mediated dopaminergic neuronal survival-promoting activity, comprising:
  a. contacting cultured dopaminergic neurons with a MANF polypeptide, wherein the amino acid sequence of the MANF polypeptide consists of a sequence at least 95% identical to SEQ ID NO: 4 and an N-terminal methionine residue;
  b. contacting the cultured dopaminergic neurons and the MANF polypeptide with a candidate compound to form a test culture;
  c. measuring MANF-mediated dopaminergic neuronal survival promoting activity in the test culture; and
  d. comparing the dopaminergic neuronal survival activity of MANF in the test culture to a control culture comprising cultured dopaminergic neurons contacted with MANF in the absence of the candidate compound,
  wherein altered MANF-mediated dopaminergic neuronal survival-promoting activity in the test culture relative to that of said control culture indicates that said candidate compound modulates MANF-mediated dopaminergic neuronal survival promoting activity.

27. The method of claim 26, wherein the N-terminal methionine residue is the N-terminal methionine residue of SEQ ID NO: 4.

* * * * *